(12) United States Patent
Delisser et al.

(10) Patent No.: US 8,101,750 B2
(45) Date of Patent: Jan. 24, 2012

(54) PROCESS FOR THE MANUFACTURING OF THE COMPOUND 2-HYDROXY-3-[5-(MORPHOLIN-4-YLMETHYL)PYRIDIN-2-YL] 1H-INDOLE-5-CARBONITRILE 701

(75) Inventors: Vern Delisser, Södertälje (SE); Martin Hedberg, Södertälje (SE); Annette Jansson, Södertälje (SE); Andreas Rådevik, Södertälje (SE); Per Ryberg, Södertälje (SE); Swantje Thiering, Gillingham Dorset (GB)

(73) Assignee: AstraZeneca AB, Sodertalje (SE)

( * ) Notice: Subject to any disclaimer, the term of this patent is extended or adjusted under 35 U.S.C. 154(b) by 23 days.

(21) Appl. No.: 12/596,020

(22) PCT Filed: Apr. 17, 2008

(86) PCT No.: PCT/SE2008/050432
§ 371 (c)(1),
(2), (4) Date: Apr. 14, 2010

(87) PCT Pub. No.: WO2008/130312
PCT Pub. Date: Oct. 30, 2008

(65) Prior Publication Data
US 2010/0286392 A1 Nov. 11, 2010

Related U.S. Application Data

(60) Provisional application No. 60/912,527, filed on Apr. 18, 2007.

(51) Int. Cl.
*C07D 295/16* (2006.01)
(52) U.S. Cl. .................................. 544/124
(58) Field of Classification Search .................. 544/124
See application file for complete search history.

(56) References Cited

U.S. PATENT DOCUMENTS

| 7,026,478 | B2 | 4/2006 | Fürstner et al. |
| 2007/0275968 | A1 | 11/2007 | Kurata et al. |
| 2009/0023732 | A1 | 1/2009 | Berg et al. |

FOREIGN PATENT DOCUMENTS

| WO | 03082853 A1 | 10/2003 |
| WO | 2005016924 A1 | 2/2005 |
| WO | 2006028029 A1 | 3/2006 |
| WO | 2007089193 A1 | 8/2007 |

OTHER PUBLICATIONS

Chen et al, "Design of 2,5-Dimethyl-3-(6-dimethyl-4-methylpyridin-3-yl)-7-dipropylaminopyrazolo[1,5-a]pyrimidine (NBI 30775/R121919) and Structure-Activity Relationships of a Series of Potent and Orally Active Corticotropin-Releasing Factor Receptor Antagonists", J.Med.Chem, 2004, 47, 4787-4798.

Chen, B et al, "New developments in hydrogenation catalysis particularly in synthesis of fine and interemediate chemicals",Applied Catalysis A: General, Elsevier Science, Amsterdam, NL LNKD-DOI:10.1016/J. APCATA.2004.08.025, vol. 280, No. 1, Feb. 25, 2005, pp. 17-46, XP004749145ISSN: 0926-860X* paragraph [01.3] *.

Maienfisch Peter et al, Azido-Neonicotinoids as Candidate Photoaffnity Probes for Insect Nicotinic Acetylcholine Receptors [1], Chimia, 2003, 57 (11), 710-714.

Petrenko, O.P. et al.: "Tautomerism of derivatives of azines. 17. Effect of solvents on the position of the azinyl-ylidene tautomeric equilibrium of substituted azinylmethanes", Journal of Heterocyclic Compounds, vol. 23, 1987, pp. 1343-1347, XP002601670 * p. 1346; compound VII *.

Selvakumar et al: "A Direct synthesis of 2-arylpropenoic acid esters having nitro groups in the aromatic ring: a short synthesis of (+/-31 )-coerulescine and (+/-31 )-horsfiline", Tetrahedron Letters, Elsevier, Amsterdam, NL LNKD-DOI: 10.1016/S0040-4039(02)02267-0, vol. 43, No. 50, Dec. 9, 2002, pp. 9175-9178, XP004391928,ISSN: 0040-4039* Scheme 3, p. 9177 *.

Tanis et al, "Synthesis and Biological Activity of Metabolites of the Antidiabetic, Antihyperglycemic Agent Pioglitazone", J. Med. Chem. 1996, 39 (26), 5053-5063.

*Primary Examiner* — Robert Havlin
(74) *Attorney, Agent, or Firm* — Kenneth F. Mitchell

(57) ABSTRACT

The present invention relates to a new process for the manufacture of the compound 2-hydroxy-3-[5-(morpholin-4-ylmethyl)pyridin-2-yl]1H-indole-5-carbonitrile as a free base and pharmaceutically acceptable salts thereof, particularly the 2-hydroxy-3-[5-(morpholin-4-ylmethyl)pyridin-2-yl] 1H-indole-5-carbonitrile citrate, and to new intermediates prepared in said process suitable for large scale manufacturing of said compound.

8 Claims, No Drawings

PROCESS FOR THE MANUFACTURING OF THE COMPOUND 2-HYDROXY-3-[5-(MORPHOLIN-4-YLMETHYL)PYRIDIN-2-YL] 1H-INDOLE-5-CARBONITRILE 701

CROSS-REFERENCE TO RELATED APPLICATIONS

This application is a US National Stage under 35 U.S.C §371 of International Application No. PCT/SE2008/050432 (filed Apr. 17, 2008) that claims the benefit under 35 U.S.C. §119(e) of Application No. 60/912,527 filed on Apr. 18, 2007.

FIELD OF THE INVENTION

The present invention relates to a new process for the manufacturing of the compound 2-hydroxy-3-[5-(morpholin-4-ylmethyl)pyridin-2-yl]1H-indole-5-carbonitrile as a free base and pharmaceutically acceptable salts thereof and to new intermediates prepared therein suitable for large scale manufacturing of said compounds.

BACKGROUND OF THE INVENTION

2-Hydroxy-3-[5-(morpholin-4-ylmethyl)pyridin-2-yl]1H-indole-5-carbonitrile as a free base and pharmaceutically acceptable salts thereof are known and useful because they possess pharmacological activity by showing inhibiting effect on GSK3 (WO 03/082853). Thus, it is expected that this compound is well suitable for prevention and/or treatment of conditions associated with cognitive disorders and predemented states, especially dementia, Alzheimer's Disease (AD), Cognitive Deficit in Schizophrenia (CDS), Mild is Cognitive Impairment (MCI), Age-Associated Memory Impairment (AAMI), Age-Related Cognitive Decline (ARCD) and Cognitive Impairement No Dementia (CIND), diseases associated with neurofibrillar tangle pathologies, Frontotemporal dementia (FTD), Frontotemporal dementia Parkinson's Type (FTDP), progressive supranuclear palsy (PSP), Pick's Disease, Niemann-Pick's Disease, corticobasal degeneration (CBDi), traumatic brain injury (TBI), dementia pugilistica, Down's syndrome, vascular dementia, Parkinson's Disease (PD), postencephelatic parkinsonism, dementia with Lewy bodies, HIV dementia, Huntington's Disease, amyotrophic lateral sclerosis (ALS), motor neuron diseases (MND, Creuztfeld-Jacob's disease, prion diseases, attention deficit disorder (ADD), attention deficit hyperactivity disorder (ADHD) and affective disorders, wherein the affective disorders are Bipolar Disorder including acute mania, bipolar depression, bipolar maintenance, major depressive disorders (MDD) including depression, major depression, mood stabilization, schizoaffective disorders including schizophrenia, dysthymia, Type I diabetes, Type II diabetes, diabetic neuropathy, alopecia, inflammatory diseases, cancer and bone-related disorders including osteoporosis.

WO 03/082853 discloses a process for the preparation of 2-hydroxy-3-[5-(morpholin-4-ylmethyl)pyridin-2-yl]1H-indole-5-carbonitrile as a free base and the hydrochloride salt thereof. In said process 5-cyanooxindole is reacted with a 2-halopyridin-N-oxide derivative in an inert organic solvent such as tetrahydrofuran, dioxane, dimethylformamide or N-methylpyrrolidin-2-one. The presence of a base is advantageous for the coupling. A temperature range of 0-130° C. was disclosed.

The N-oxide could be removed with phosphorus trichloride in a suitable solvent such as methylene chloride, toluene or ethyl acetate to furnish 2-hydroxy-3-[5-(morpholin-4-ylmethyl)pyridin-2-yl]1H-indole-5-carbonitrile. In the disclosed process the 5-cyanooxindole is expensive and is not available as a commercial bulk substance. At the temperature for the coupling, 130° C., the starting 5-cyanooxindole decomposes. The use of N-oxides on large scale is of concern due to their potential explosive properties. Purification to achieve a pharmaceutically acceptable quality material could only be achieved by column chromatography. This purification technique is not the most practical or economical for large-scale manufacture. In addition, upon scale up low yields where obtained.

In summary, there is a need for a more convenient and more economically efficient process for the manufacturing of 2-hydroxy-3-[5-(morpholin-4-ylmethyl)pyridin-2-yl]1H-indole-5-carbonitrile as a free base and pharmaceutically acceptable salts thereof, especially with regard to large-scale production where factors like costs, manufacturing time, robustness and safety are vital for commercial application. The present invention provides for such a process.

BRIEF DESCRIPTION OF THE INVENTION

The present invention is directed to a new process for manufacturing of the compound (2-hydroxy-3-[5-(morpholin-4-ylmethyl)pyridin-2-yl]1H-indole-5-carbonitrile as a free base and pharmaceutically acceptable salts thereof, particularly the citrate salt.

Further, it provides for a new process to prepare novel compounds, which are useful as intermediates in the preparation of said pharmaceutically active compound. Example of such new intermediates are methanesulfonic acid 6-methyl-pyridin-3-ylmethyl ester, 4-(6-methyl-pyridin-3-ylmethyl)-morpholine, (5-morpholin-4-ylmethyl-pyridin-2-yl)-acetic acid ethyl ester, (5-cyano-2-nitro-phenyl)-(5-morpholin-4-ylmethyl-pyridin-2-yl)-acetic acid ethyl ester, (2-amino-5-cyano-phenyl)-(5-morpholin-4-ylmethyl-pyridin-2-yl)-acetic acid ethyl ester; 2-ethoxy-3-(5-morpholin-4-ylmethyl-pyridin-2-yl)-1H-indole-5-s carbonitrile and 1-hydroxy-3-(5-morpholin-4-ylmethyl-pyridin-2-yl)-2-oxo-2,3-dihydro-1H-indole-5-carbonitrile.

DESCRIPTION OF THE INVENTION

The new manufacturing processes of the present invention may be described in the to following way:

Scheme 1

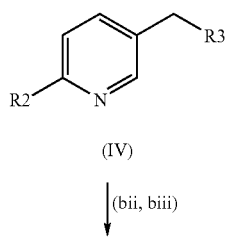

(IV)

(bii, biii)

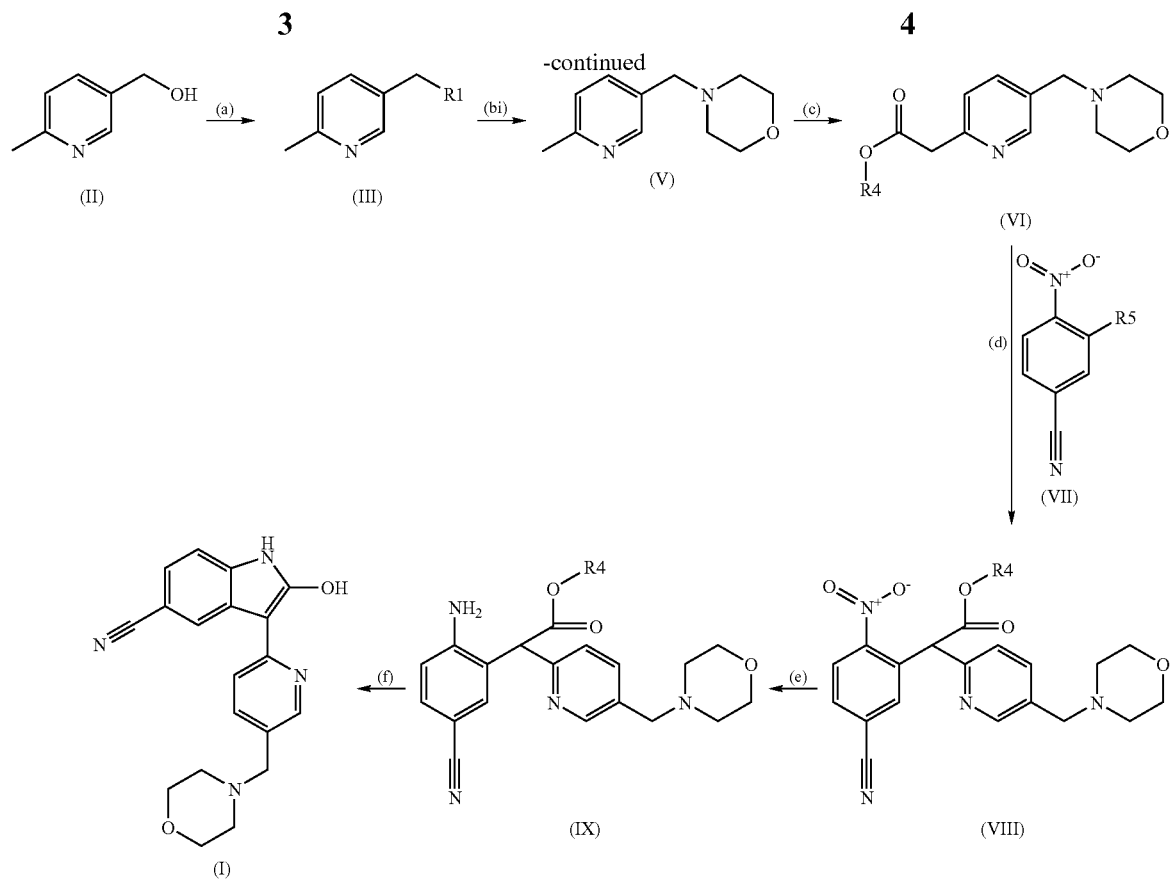

A. A process for the preparation of 2-hydroxy-3-[5-(morpholin-4-ylmethyl)pyridin-2-yl]1H-indole-5-carbonitrile as a free base and pharmaceutically acceptable salts thereof, by a) reacting a compound of formula (II) with a compound of formula $R_6SO_2X$ wherein $R_6$ is $C_1$-$C_4$ alkyl, $C_1$-$C_4$ alkylphenyl, phenyl, phenylmethyl, halophenyl, nitrophenyl or $CF_3$, particularly methyl, and X is halogen, particularly chloro, in the presence of a solvent and a base to give a compound of formula (III), wherein $R_1$ is $R_6SO_3$, where $R_6$ is $C_1$-$C_4$ alkyl, $C_1$-$C_4$ alkylphenyl, tolyl, phenyl, phenylmethyl, halophenyl, nitrophenyl or $CF_3$, particularly methyl, which either is isolated or, followed by bi) reacting the compound of formula (III) wherein $R_1$ is as defined above in the presence of morpholine optionally with a base and in a solvent to obtain a compound of formula (V)

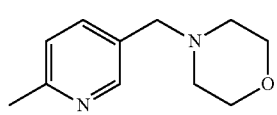
(V)

which either is isolated or followed directly by step c) below.

Alternative ways for preparation of a compound of formula (V) are described below:

bii) reacting a compound of formula (IV), wherein R2 is methyl and R3 is a halogen in a solvent with morpholine optionally with a base to obtain compound of formula (V)

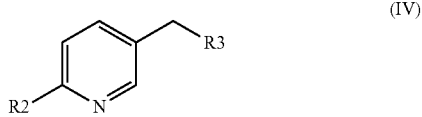
(IV)

which may be isolated, or biii) reacting a compound of formula (IV) wherein $R_2$ is halogen and $R_3$ is morpholine attached at nitrogen

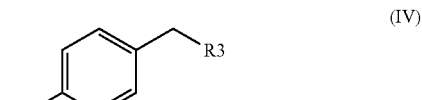
(IV)

with methylmagnesium halide in the presence of iron (2,4-pentanedionate)$_3$ in a solvent to obtain a compound with formula (V)

followed by, c) reacting a compound of formula (V)

with a carbonate of formula (X) or a dicarbonate of formula (XI)

(X)

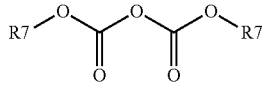

wherein R₄ is independently selected from an $C_{1-12}$alkyl or aryl-$C_{1-4}$alkyl group and R7 is an tert-butyl group in a solvent in the presence of a base to give a compound of formula (VI) which either is isolated, or its enolate is reacted further

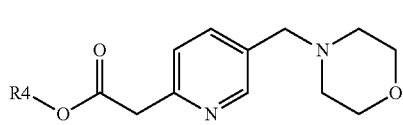

by, d) reacting the compound of formula (VI) wherein R₄ is $C_{1-12}$alkyl or aryl-$C_{1-4}$alkyl with a compound of formula (VII), where R₅ is a hydrogen or a halogen

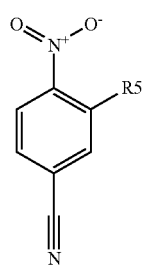

in the presence of a base and a solvent, to form a compound of formula (VIII) wherein R₄ is $C_{1-12}$alkyl or aryl-$C_{1-4}$alkyl, which either is isolated, or

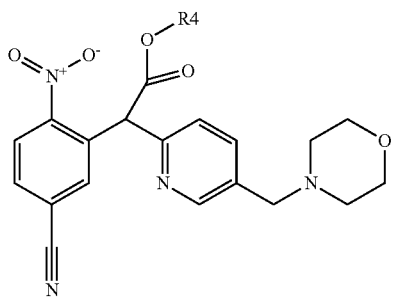

followed by, e) reducing the compound of formula (VIII) wherein R₄ is $C_{1-12}$alkyl or aryl-$C_{1-4}$alkyl with a suitable reducing agent in the presence of a solvent to selectively reduce the nitro group to an amine in the presence of the other functional groups to obtain a compound of formula (IX) wherein R₄ is $C_{1-12}$alkyl or aryl-$C_{1-4}$alkyl, which either is isolated, or followed by,

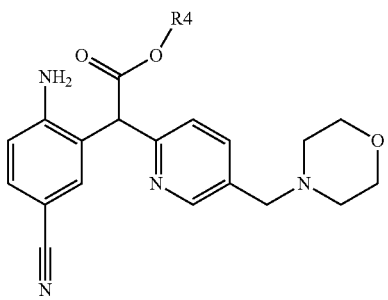

f) cyclisation of the compound of formula (IX) wherein R₄ is $C_{1-12}$alkyl or aryl-$C_{1-4}$alkyl with an acid or a base to obtain a compound of formula (I), the 2-hydroxy-3-[5-(morpholin-4-ylmethyl)pyridin-2-yl]1H-indole-5-carbonitrile as a free base or a pharmaceutically acceptable salt thereof, which is purified and isolated to obtain the pure compound (1) as a free base or pharmaceutically acceptable salt thereof.

B. Another alternative for process steps e) and f) above in the new manufacturing process for the preparation of 2-hydroxy-3-[5-(morpholin-4-ylmethyl)pyridin-2-yl]1H-indole-5-carbonitrile as a free base and pharmaceutically acceptable salts thereof, may be described in the following way:

Scheme 2

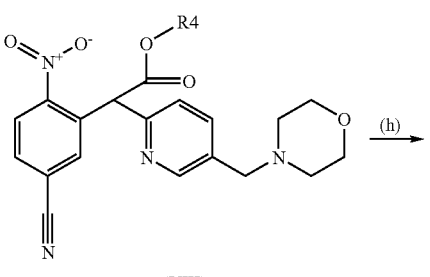

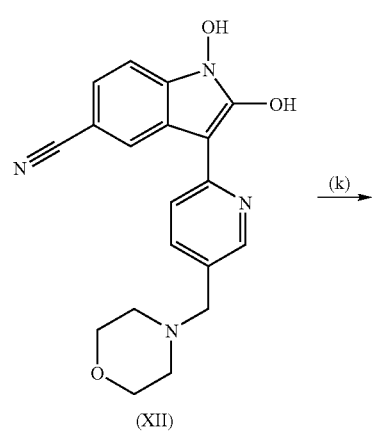

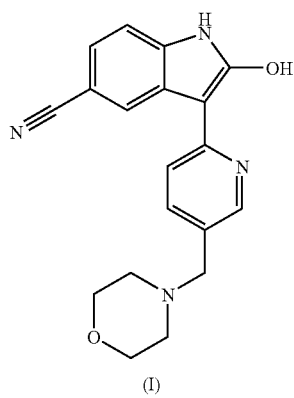

(I)

by h) treating a compound of formula (VIII) wherein $R_4$ is $C_{1-12}$alkyl or aryl-$C_{1-4}$alkyl with a suitable reducing agent in a solvent to form a compound of formula (XII), followed by k) reducing the hydroxamic acid group in the compound of formula (XII) by treating with a suitable reducing agent in a solvent to obtain a compound of formula (I), the 2-hydroxy-3-[5-(morpholin-4-ylmethyl)pyridin-2-yl]1H-indole-5-carbonitrile, as a free base or a pharmaceutically acceptable salt thereof, which is purified and isolated to obtain the pure free base or pharmaceutically acceptable salt thereof.

C. Yet another alternative process step f) above in the new manufacturing process for the preparation of 2-hydroxy-3-[5-(morpholin-4-ylmethyl)pyridin-2-yl]1H-indole-5-carbonitrile as a free base and pharmaceutically acceptable salts thereof, may be described in the following way:

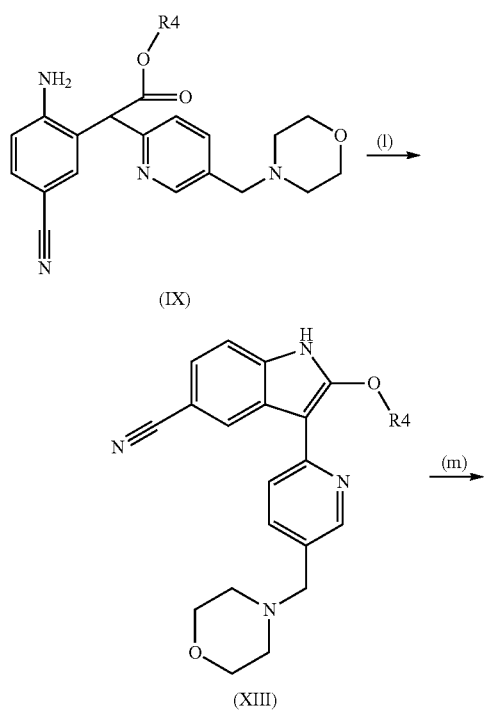

Scheme 3

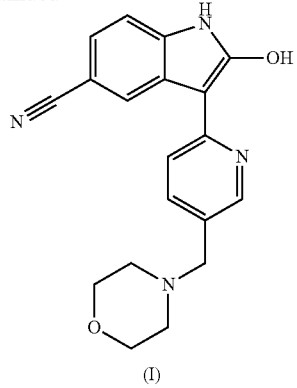

(I)

by l) reacting the compound of formula (IX) wherein $R_4$ is $C_{1-12}$alkyl or aryl-$C_{1-4}$alkyl with a suitable acid in a solvent to form a compound of formula (XIII) wherein $R_4$ is $C_{1-12}$alkyl or aryl-$C_{1-4}$ alkyl, followed by m) reacting the compound of formula (XIII) with a suitable acid in a solvent to obtain a is compound of formula (I), the 2-hydroxy-3-[5-(morpholin-4-ylmethyl)pyridin-2-yl]1H-indole-5-carbonitrile, as a free base or a pharmaceutically acceptable salt thereof, which is purified and isolated to obtain the pure free base or pharmaceutically acceptable salt thereof.

DETAILED DESCRIPTION OF THE INVENTION

A. A manufacturing process for the preparation of 2-hydroxy-3-[5-(morpholin-4-ylmethyl)pyridin-2-yl]1H-indole-5-carbonitrile as a free base and pharmaceutically acceptable salts thereof, by:

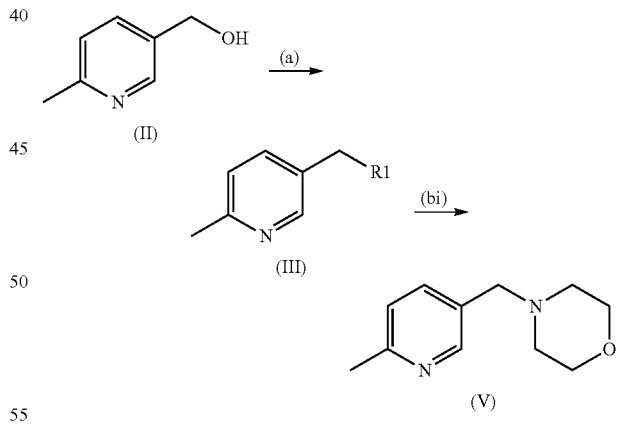

Scheme 4 a) reacting a compound of formula (II) with a compound of formula $R_6SO_2X$, wherein $R_6$ is $C_1$-$C_4$ alkyl, $C_1$-$C_4$alkylphenyl, phenyl, phenylmethyl, halophenyl, nitrophenyl or $CF_3$, particularly methyl, and X is halogen, particularly chloro, in the presence of a solvent and a base to give a compound of formula (III), wherein $R_1$ is $R_6SO_3$, where $R_6$ is $C_1$-$C_4$alkyl, $C_1$-$C_4$alkylphenyl, phenyl, phenylmethyl, halophenyl, nitrophenyl or $CF_3$, particularly methyl which either is isolated or, followed by bi) reacting the compound of formula (III) wherein $R_1$ is as defined above in the presence of morpholine optionally with a base and in a solvent to obtain a compound of formula (V) which either is isolated or followed directly by step c) below.

The starting compound of formula (II) may be prepared in a known manner described in the prior art (J. Med. Chem. 1996, 39 (26), 5053).

The reaction steps a) and bi) may be performed in a solvent. Suitable solvents are ethers such as tetrahydrofuran, methyltetrahydrofuran, diethyleneglycol dimethyl ether, cyclopentyl methyl ether or 1,4-dioxane, or a polar aprotic solvent such as N,N-dimethylacetamide, N-methyl-2-pyrrolidinone, dimethylformamide, 1,3-dimethyltetrahydro-2(1H)-pyrimidinone, dimethylsulphoxide or tetramethyl urea, aromatic hydrocarbons such as toluene or xylene, halogenated solvents such as dichloromethane, chloroform or dichloroethane or nitriles eg acetonitrile, propionitrile or mixtures thereof, particularly tetrahydrofuran.

The total amount of solvents used in the coupling process a), may vary in the range of about 2 to 100 (v/w) volume parts per weight of starting material, particularly in the range of about 5 to 30 (v/w) volume parts per weight of starting material.

A suitable base may be an organic amine base such as triethylamine, diisopropylethylamine, pyridine, dimethylaminopyridine or alkali metal salts such as sodium carbonate, particularly triethylamine.

The amount of base used in the coupling process a) may vary in the range from about 1 to 5 mole equivalents of compound of formula (II).

The temperature of the coupling step a) may be in the range of about −80° C. to +60° C., particularly in the range of about −10° C. to room temperature.

The mole equivalent of $R_6SO_2X$ compared to compound of formula (II) may be in the range of about 1 and 5 mole equivalents, particularly in the range of about 1 and 2 mole equivalents.

The total amount of solvents used in the coupling process step bi) may vary in the range of about 2 to 100 (v/w) volume parts per weight of starting material, particularly in the range of about 5 to 30 (v/w) volume parts per weight of starting material.

A suitable base to be used in step bi) may be an organic amine base such as, triethylamine, diisopropylethylamine, pyridine, dimethylaminopyridine, morpholine or alkali metal salts such as sodium carbonate, particularly morpholine.

The amount of base used in step bi) may vary in the range of about 1 to 5 mole equivalents of compound of formula (III).

The temperature of the coupling step bi) may be in the range of about −20° C. to +60° C.

The compound of formula (V) has a chromatographic purity of at least 90%, preferably more than 95%.

An alternative way for preparation of a compound of formula (V) is by:

bii) reacting a compound of formula (IV), wherein $R_2$ is methyl and $R_3$ is a halogen in a solvent with morpholine optionally with a base to obtain compound of formula (V) which may be isolated.

The starting compound of formula (IV) wherein $R_2$ is methyl and $R_3$ is chloro may be prepared in a known manner described in the prior art (J. Med. Chem, 2004, 47(11), 4787) and the bromo analogue may be synthesized as disclosed in WO2005016924.

Suitable solvents in bii) are ethers such as tetrahydrofuran, methyltetrahydrofuran, diethyleneglycol dimethyl ether, cyclopentyl methyl ether or 1,4-dioxane, or a polar aprotic solvent such as N,N-dimethylacetamide, N-methyl-2-pyrrolidinone, dimethylformamide, 1,3-dimethyltetrahydro-2 (1H)-pyrimidinone, dimethylsulphoxide or tetramethyl urea, aromatic hydrocarbons such as toluene or xylene, halogenated solvents such as dichloromethane, chloroform or dichloroethane or nitriles such as acetonitrile, propionitrile or mixtures thereof, particularly toluene.

The total amount of solvents used may vary in the range of about 2 to 100 (v/w) volume parts per weight of starting material, particularly in the range of about 3 to 30 (v/w) volume parts per weight of starting material.

A suitable base may be an organic amine base such triethylamine, diisopropylethylamine, morpholine or alkali metal salts such as sodium carbonate, particularly morpholine.

The amount of base may vary in the range of about 1 to 5 mole equivalents of the compound of formula (IV), particularly in the range of about 2 to 3 mole equivalents of the compound of formula (IV).

The reaction may also be carried out using morpholine acting as solvent and base.

The temperature of the coupling step bii) may be in the range of about 0° C. to +70° C.

The compound of formula (IV) has a chromatographic purity of at least 90%, preferably more than 95%.

Another alternative way for preparation of a compound of formula (V) is by:

biii) reacting a compound of formula (IV) wherein $R_2$ is halogen, particularly chloro, and $R_3$ is morpholine attached at nitrogen, with a methylmagnesium halide in the presence of iron 2,4-pentanedionate in a solvent to obtain a compound of formula (V).

The starting compound of formula (IV) wherein $R_3$ is morpholine and $R_2$ is halogen, where the halogen is chloro may be prepared in the known manner described in the prior art (Chimia, 2003, 57 (11), 710), and when halogen is bromo it may be prepared in a known manner described in WO2006028029. A reaction of a compound (IV) defined as above with methylmagnesium halide in the presence of iron (2,4-pentanedionate)$_3$ in a solvent is done in accordance with the reaction prior described in U.S. Pat. No. 7,026,478.

Step c) describes the manufacturing process of a compound of formula (VI) wherein $R_4$ is a $C_{1-12}$ alkyl or aryl-$C_{1-4}$ alkyl

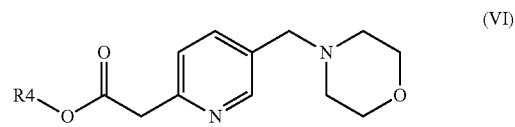

(VI)

and it is carried out by reacting a compound of formula (V), 4-(6-methyl-pyridin-3-ylmethyl)-morpholine, with a carbonate of formula (X), wherein $R_4$ is independently selected from an $C_{1-12}$alkyl group or aryl-$C_{1-4}$alkyl, or a dicarbonate of formula (XI) wherein $R_7$ is tert-butyl, in the presence of base in a solvent. A carbonate is of particular interest.

(X)

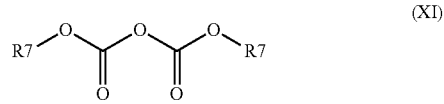

(XI)

A suitable organic solvent is a mixture of a polar aprotic solvent, which may be selected from the group comprising of sulpholane, tetramethylurea or 1,3-dimethyl-2-imidazolidinone or ethers such as tetrahydrofuran, 2-methyl tetrahydrofuran, dioxane, tert-butlymethyl ether, cyclopentyl methyl ether, or diethyleneglycol dimethyl ether or aromatic hydrocarbons such as toluene, xylene, and/or aliphatic hydrocarbons such as hexanes, heptanes or octanes or mixture thereof. A particularly suitable solvent is tetrahydrofuran.

The reaction may be performed without a solvent particularly when using compounds of formula (X).

A suitable base may be an organic amine base such as diazabicyclo[5.4.0]undec-7-ene, $C_{1-6}$alkyl lithium, alkali metal hydrides such as sodium hydride and lithium hydride; or alkali metal amides such as lithium diisopropylamide, sodium diisopropylamide or sodium amide, particularly lithium diisopropylamide.

The amount of base used in the coupling process step may vary in the range of about 1 to 5 mole equivalents of compound of formula (V), particular between about 2 to 3 equivalents.

The total amount of solvents may vary in the range of about 1 to 100 (v/w) volume parts per weight of starting material, particularly in the range of about 5 to 20 (v/w) volume parts per weight of starting material.

The temperature used in process c) may be in the range of about −100° C. to +100° C., particularly in the range of about −30° C. to +50° C.

The work up may in general be performed by methods known by someone skilled in the art, for example by extraction and optional filtration, chromatographic purification and/or crystallization to obtain the compounds of formulae (I), (V), (VI), (VIII), (IX), (XII) and (XIII).

Compounds of formula (VI) are normally obtained with a purity of at least 90%, preferably more than 95% and may be used directly as a solution in the following step d).

The reaction step d) of the manufacturing process of a compound of formula (VIII), wherein $R_4$ is a $C_{1-12}$alkyl or aryl-$C_{1-4}$alkyl

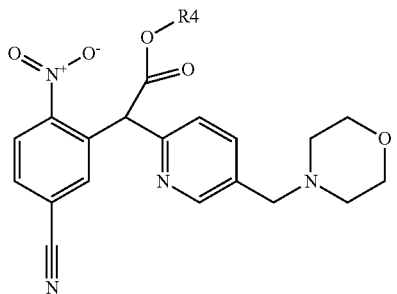

(VIII)

is carried out by reacting a compound of formula (VI) wherein $R_4$ is a $C_{1-12}$alkyl or aryl-$C_{1-4}$alkyl with a compound of formula (VII), wherein $R_5$ is hydrogen or halogen, particularly fluoro, in the presence of a base in a solvent

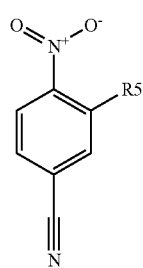

(VII)

The compound of formula (VII), wherein $R_5$ is hydrogen and when $R_5$ is fluoro are commercially available.

A suitable base may be alkali metal hydrides such as sodium hydride and lithium hydride; or alkali metal amides such as, sodium bis(trimethylsilyl) amide, lithium diisopropylamide or sodium amide or alkoxides such as lithium tert-butoxide or potassium tert-butoxide, particularly lithium tert-butoxide.

The amount of base used in the process step d) may vary in the range of about 1 to 5 mole equivalents of compound of formula (VI), particularly in the range of about 2 to 3 mole equivalents of compound of formula (VI).

Suitable solvents are ethers such as tetrahydrofuran, 2-methyl tetrahydrofuran, dioxane tert-butlymethyl ether, cyclopentyl methyl ether, or diethyleneglycol dimethyl ether, or aromatic hydrocarbons such as toluene, or mixtures thereof. The particularly suitable solvent is tetrahydrofuran.

The total amount of solvents may vary in the range of about 1 to 100 (v/w) volume parts per weight of starting material, particularly in the range of about 5 to 20 (v/w) volume parts per weight of starting material.

The temperature used in process c) may be in the range of about −100° C. to +100° C., particularly in the range of about −30° C. to +50° C.

The reaction is performed with or without bubbling an inert gas through the reaction mixture, preferably with an inert gas such as nitrogen, argon or helium, preferably nitrogen, excluding air/oxygen.

The work up may be performed by methods known by someone skilled in the art as earlier described, optionally to improve phase separation during extraction a filtering aid may be added to the entire two phase system before filtration and phase separation.

Compound of formula (VIII) may be isolated as an oil, a solid or may be converted to an appropriate salt using both organic acids e.g. p-toluenesulphonic acid, methanesulphonic acid, benzoic acid or inorganic acids e.g. hydrochloric acid, or sulphuric acid, particularly hydrochloric acid, in a solvent.

Suitable solvents for the salt formation are ethers such as tetrahydrofuran, 2-methyl tetrahydrofuran, dioxane, tert-butlymethyl ether, cyclopentyl methyl ether or diethyleneglycol dimethyl ether, aromatic hydrocarbons such as toluene, xylene, and/or aliphatic hydrocarbons such as hexanes, heptanes or octanes, aliphatic alcohols such as ethanol, methanol or isopropanol, esters such as ethyl acetate or butylacetate, or mixtures of the above solvents, particularly a mixture of n-butyl acetate and ethanol.

Suitable solvent for the isolation of compound of formula (VIII) as a crystalline free base are esters such as ethyl acetate or butylacetate; aliphatic alcohols such as ethanol, methanol or isopropanol, and/or aliphatic hydrocarbons such as hexanes, heptanes or octanes; particularly n-butylacetate and heptane.

Compounds of formula (VIII) are normally obtained with a purity of at least 90%, preferably more than 95%

The reaction step e) of the manufacturing process for a compound of formula (IX), wherein $R_4$ is a $C_{1-12}$alkyl or aryl-$C_{1-4}$alkyl

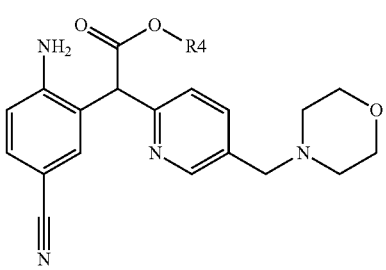

(IX)

may be carried out by reduction of the nitro group in compounds of formula (VIII) with a suitable reducing agent in a solvent in the known manner described in for instance "Comprehensive Organic Transformations;" R. C. Larock., VCH publishers; ISBN 0-89573-710-8, Edition 2, page 823".

A particularly suitable reducing agent may be hydrogenation using molecular hydrogen and a metal catalyst such as palladium on carbon or platinum/vanadium on carbon.

The reaction may be performed in a solvent. Suitable solvents are mixtures of polar aprotic solvents e.g. N,N-dialkylamides such as N,N-dimethylformamide, N,N-dimethylacetamide, N-methylpyrrolidinone and dimethylsulphoxide, ethers such as tetrahydrofuran or 1,4-dioxane or methyltetrahydrofuran, cyclopentyl methyl ether, nitriles such as acetonitrile or propionitrile, esters such as butyl acetate or aromatic such as toluene, xylene, alcohols such as methanol, ethanol or butanol, and/or water. Particularly suitable solvents are N,N-dimethylformamide, toluene, butyl acetate or mixtures thereof. A particularly suitable solvent is n-butyl acetate.

The total volume of solvents used may be in the range of about 1 to 100 (v/w) volume parts per weight of starting material, particularly in the range of about 2 to 40 (v/w) volume parts per weight of starting material.

The ratio of catalyst to compound of formula (VIII) may be in the range of about 1 (w/w %) and 100 (w/w %), particularly in the range of about 1 (w/w %) and 30 (w/w %).

The temperature of the reaction may be in the range of about room temperature and +150° C., particularly in the range of about +35° C. and +100° C.

The pressure may be in the range of about 1 and 20 bar, particularly in the range of about between atmospheric and 5 bar.

Compounds of formula (IX) are normally obtained with a purity of at least 80%.

The reaction step f) of the manufacturing process of a compound of formula (I), 2-hydroxy-3-[5-(morpholin-4-ylmethyl)pyridin-2-yl]1H-indole-5-carbonitrile as the free base or pharmaceutically acceptable salts thereof, particularly the citrate salt

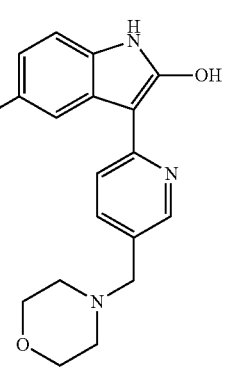

(I)

is carried out by reacting compounds of formula (IX), wherein $R_4$ is a is $C_{1-2}$alkyl or aryl-$C_{1-4}$alkyl with an acid in a solvent.

The acid may be selected from organic acids such as acetic acid, methanesulphonic acid, toluenesulphonic acid, citric acid or inorganic acids such as hydrochloric acid, sulphuric acid or phosphoric acid, particularly hydrochloric and citric acid.

The suitable number of mole equivalents of acid is in the range of about 1 to 4 mole equivalents in relation to compound of formula (IX), particularly in the range of about 1 to 3 equivalents.

The reaction may be performed in a solvent. Suitable solvents are mixtures of polar aprotic solvents e.g. N,N-dialkylamides such as N,N-dimethylformamide, N,N-dimethylacetamide, N-methylpyrrolidinone and dimethylsulphoxide, ethers such as tetrahydrofuran, cyclopentyl methyl ether, 1,4-dioxane, ketones such as methyl iso-butyl ketone, nitriles such as acetonitrile or propionitrile, aromatic hydrocarbons such as toluene or xylene, alcohols such as methanol, ethanol, isopropanol or butanol, esters such as ethyl acetate, isopropyl acetate or butyl acetate, organic acids such as acetic acid and/or water. Particularly suitable solvents are a mixture of toluene and dimethylformamide, or butyl acetate and dimethylformamide. A particularly suitable solvent is a mixture of N,N-dimethylformamide and n-butyl acetate.

The total volume of solvents used may be in the range of about 1 to 100 (v/w) volume parts per weight of starting material, particularly in the range of about 2 to 40 (v/w) volume parts per weight of starting material.

The temperature of the reaction may be in the range of about room temperature and +150° C., particularly in the range of about +60° C. and +100° C.

Alternatively the reaction step f) of the manufacturing process of a compound of formula (I), 2-hydroxy-3-[5-(morpholin-4-ylmethyl)pyridin-2-yl]1H-indole-5-carbonitrile as the free base may be carried out by reacting compounds of formula (IX), wherein $R_4$ is a $C_{1-12}$alkyl or aryl-$C_{1-4}$alkyl with a base in a solvent. Examples of suitable bases are an organic amine base e.g. triethylamine or an alkali metal salt such as potassium carbonate, but not limited thereto.

The suitable number of mole equivalents of base is in the range of about 0.1 to 4 mole equivalents in relation to compound of formula (IX), particularly in the range of about 0.1 to 2 equivalents.

The reaction may be performed in a solvent Suitable solvents are mixtures of polar aprotic solvents e.g. N,N-dialkylamides such as N,N-dimethylformamide, N,N-dimethylacetamide, N-methylpyrrolidinone and dimethylsulphoxide, ethers such as tetrahydrofuran, cyclopentyl methyl ether, 1,4-dioxane, ketones such as methyl iso-butyl ketone, nitriles such as acetonitrile or propionitrile, aromatic hydrocarbons such as toluene or xylene, alcohols such as methanol, ethanol, isopropanol or butanol, esters such as ethyl acetate, isopropyl acetate or butyl acetate and/or water or mixtures thereof.

The total volume of solvents used may be in the range of about 1 to 100 (v/w) volume parts per weight of starting material, particularly in the range of about 2 to 40 (v/w) volume parts per weight of starting material.

The temperature of the reaction may be in the range of about +20° C. and +110° C., particularly in the range of about +60° C. and +100° C.

Compounds of formula (I) or salts thereof are normally obtained with a purity of at least 90%, preferably more than 95%.

In step f) of the manufacturing process of the compound (1), 2-hydroxy-3-[5-(morpholin-4-ylmethyl)pyridin-2-yl]1H-indole-5-carbonitrile as the free base or as a pharmaceutically acceptable salt thereof, particularly the citrate salt, of pharmaceutical purity is prepared by treating its solution with/or without a metal scavenger.

Suitable metal scavengers are an organo-functionalised polysiloxane or polymer or activated carbon or a mixture thereof, particularly activated carbon.

The amount of scavenger to compound of formula (I) may be in the range of about 10% (w/w) and 100% (w/w), particularly in the range of about 10% (w/w) and 50% (w/w).

The purification step may be performed in a solvent, which is a mixture of water and ethers such as 1,4-dioxane or tetrahydrofuran or alcohols such as methanol, ethanol or isopropanol, ketones such as acetone or organic acids such as acetic acid, particularly mixtures of water and/or acetone and/or ethanol.

The total volume of solvents used may be in the range of about 1 (v/w) to 100 (v/w) volume parts per weight of the salt of compound (1), particularly in the range of about 10 (v/w) and 45 (v/w) volumes parts per weight of the salt of compound (1).

The temperature of the scavenger treatment may be in the range of about room temperature and +110° C.

Pure compound of formula (I), 2-hydroxy-3-[5-(morpholin-4-ylmethyl)pyridin-2-yl]1H-indole-5-carbonitrile as the free base or pharmaceutically acceptable salt thereof, particularly the citrate salt, may be obtained by crystallisation with or without an additive in suitable solvents to obtain a crystalline solid having a purity of about 95% and preferably about 98%.

B. An alternative synthesis of a compound of formula (I), 2-hydroxy-3-[5-(morpholin-4-ylmethyl)pyridin-2-yl]1H-indole-5-carbonitrile may be by h) reduction of the nitro group in a compound of formula (VIII) wherein $R_4$ is a $C_{1-12}$alkyl or aryl-$C_{1-4}$ alkyl with a suitable reducing agent in a solvent to obtain a compound of formula (XII) followed by k) reduction of the compound of formula (XII) with a suitable reducing agent in a solvent to obtain 2-hydroxy-3-[5-(morpholin-4-ylmethyl)pyridin-2-yl]1H-indole-5-carbonitrile (Scheme 2).

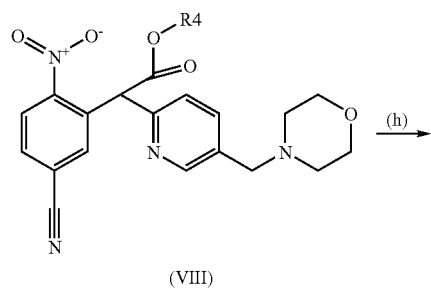

(VIII)

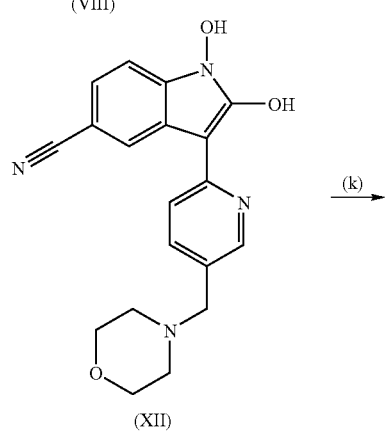

(XII)

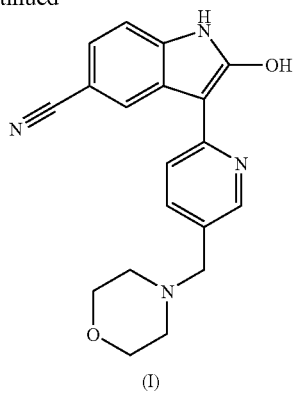

(I)

In step h) and k) a suitable reducing agent may be iron in acetic acid, zinc in acetic acid, titanium trichloride, ammonium sulphide, or hydrogenation using a metal catalyst e.g. palladium on carbon, platinum/vanadium on carbon, Raney-nickel.

Suitable solvents in these reaction steps h) and k) may be polar aprotic solvents e.g. N,N-dialkylamides such as N,N-dimethylformamide, N,N-dimethylacetamide, N-methylpyrrolidinone and dimethylsulphoxide, ethers such as tetrahydrofuran, cyclopentyl methyl ether or 1,4-dioxane, ketones methyl iso-butyl ketone, nitriles such as acetonitrile or propionitrile, aromatic hydrocarbons such as toluene, xylene, or alcohols such as methanol, ethanol or butanol or organic acids such as acetic acid or water or mixtures thereof.

The total volume of solvents used may vary in the range of about 1 to 100 (v/w) volume parts per weight of starting material, particularly in the range of about 2 to 40 (v/w) volume parts per weight of starting material.

The temperature of the reaction may be in the range of about room temperature and +150° C., particularly in the range of about room temperature and +100° C.

Compounds of formula (I) are normally obtained with a purity of at least 90%, particularly more than 95%.

Pure compound of formula (I), 2-hydroxy-3-[5-(morpholin-4-ylmethyl)pyridin-2-yl]1H-indole-5-carbonitrile as the free base or pharmaceutically acceptable salt thereof, particularly the citrate salt, may be obtained by crystallisation with or without an additive in suitable solvents to obtain a crystalline solid having a purity of about 95% and preferably about 98%.

C. Another alternative synthesis of compound of formula (I), 2-hydroxy-3-[5-(morpholin-4-ylmethyl)pyridin-2-yl] 1H-indole-5-carbonitrile may be by l) cyclisation of a compound of formula (IX) wherein $R_4$ is a $C_{1-12}$alkyl or aryl-$C_{1-4}$ alkyl with a suitable acid in a solvent to obtain a compound of formula (XIII), followed by m) reaction of the compound of formula (XIII) wherein $R_4$ is a $C_{1-12}$alkyl or aryl-$C_{1-4}$ alkyl with a suitable acid in a solvent

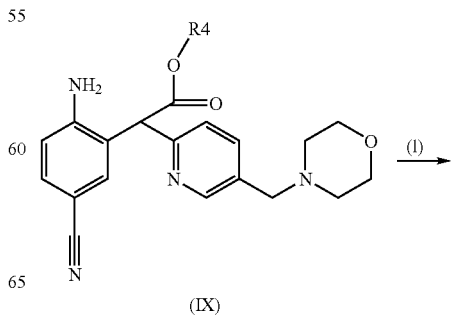

(IX)

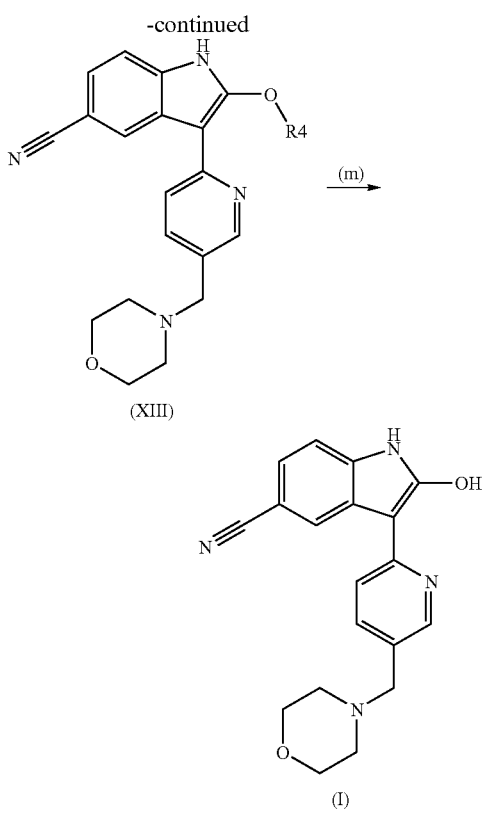

Suitable acids to be used in reaction steps l) and m) are organic acids such as acetic acid, methanesulphonic acid, toluenesulphonic acid, citric acid or inorganic acids such as hydrochloric acid, sulphuric acid or phosphoric acid, particularly citric acid.

The equivalent of acid to compound of formula (IX) and (XIII) may be in the range from about 1 to 4 mole equivalents, particularly from about 1 to 3 equivalents.

Suitable solvents to be used in reaction steps l) and m) are mixtures of polar aprotic solvents e.g. N,N-dialkylamides such as N,N-dimethylformamide, N,N-dimethylacetamide, N-methylpyrrolidinone and dimethylsulphoxide, ethers such as tetrahydrofuran, methyltetrahydrofuran, cyclopentyl methyl ether or 1,4-dioxane, ketones such as methyl iso-butyl ketone, nitriles such as acetonitrile or propionitrile, aromatic hydrocarbons such as toluene, xylene, or alcohols such as methanol, ethanol, isopropanol or butanol or organic acids such as acetic acid or inorganic acids such as hydrochloric acid and sulphuric acid, and water. A particularly suitable solvent is a mixture of toluene and N,N-dimethylformamide.

The temperature of the reaction in step l) may be in the range of about room temperature to +100° C., particularly in the range of about room temperature to +60° C.

The temperature of the reaction in step m) may be in the range of about room temperature to +150° C., particularly in the range of about 70° C. to +110° C.

Compounds of formula (I) are normally obtained with a purity of at least 90%, particularly more than 95%.

Pure compound of formula (I), 2-hydroxy-3-[5-(morpholin-4-ylmethyl)pyridin-2-yl]1H-indole-5-carbonitrile as the free base or pharmaceutically acceptable salt thereof, particularly the citrate salt, may be obtained by crystallisation with or without an additive in suitable solvents to obtain a crystalline solid having a purity of about 95% and preferably about 98%.

In the context of this specification and claims, unless otherwise stated, the terms have the definitions as follows:

The term $C_{1-12}$ alkyl includes both straight and branched chain as well as cyclic alkyl groups having 1 to 12 carbon atoms and may be, but is not limited to, methyl, ethyl, n-propyl, i-propyl, n-butyl, i-butyl, s-butyl, t-butyl, n-pentyl, i-pentyl, t-pentyl, neo-pentyl, n-hexyl, i-hexyl cyclohexyl, heptyl, octyl nonyl, decyl, undecyl or dodecyl.

The term $C_{1-4}$alkyl includes both straight and branched chain having 1 to 4 carbon atoms and may be, but is not limited to, methyl, ethyl, n-propyl, i-propyl, n-butyl, i-butyl, s-butyl and t-butyl.

The term aryl-$C_{1-4}$ alkyl includes both substituted and unsubstituted aryls, and may be, but is not limited to, benzyl and 4-methoxybenzyl.

The terms halo and halogen includes chloro, fluoro, bromo and iodo.

The term "room temperature" means a temperature between 18° C. and 25° C.

The term "large scale" means a manufacturing scale in the range of about 10 gram to 1 ton.

The skilled person will appreciate that the different reaction steps need different reaction times as well as that the different compounds obtained in the different reaction steps can be isolated or used in-situ in next step.

The new large scale manufacturing process described herein is more advantageous than the known processes with respect to commercial potential, costs, manufacturing time, safety, yield, and robustness. In a process of the present invention the use of potential explosive intermediates such as pyridine-N-oxides is avoided.

Yet another object of the present invention is the reaction of a compound of formula (VI), wherein $R_4$ is $C_{1-12}$alkyl or aryl-$C_{1-4}$alkyl, particularly $R_4$ is $C_{1-4}$alkyl, preferably ethyl, with a compound of formula (VII), wherein $R_5$ is hydrogen or halogen, particularly the 3-fluoro-4-nitrobenzonitrile, in the presence of a suitable base in a solvent to obtain a compound of formula (VIII), wherein $R_4$ is defined as above; (step d in Scheme 1).

Yet another object of the present invention is the selective reduction of the nitro functional group in a compound of formula (VIII), wherein $R_4$ is $C_{1-12}$alkyl or aryl-$C_{1-4}$alkyl, particularly $R_4$ is $C_{1-4}$alkyl, preferably ethyl, with a suitable reducing agent in the presence of a solvent, to form a compound of formula (IX), wherein $R_4$ is defined as above; (step e in Scheme 1).

Suitable reducing agent may be hydrogenation using platinum/vanadium on carbon as catalyst.

Yet another object of the present invention is the cyclisation of a compound of formula (IX), wherein $R_4$ is $C_{1-12}$alkyl or aryl-$C_{1-4}$alkyl, particularly $R_4$ is $C_{1-4}$alkyl, particularly to ethyl, with a suitable acid in a solvent to obtain a compound of the formula (I); (step f in Scheme 1).

Novel Intermediates

The present invention is also directed to new intermediates, namely intermediates of is formulae (V), (VI), (VIII), (IX), (XII) and (XIII).

A compound of formula (V), named 4-(6-methyl-pyridin-3-ylmethyl)-morpholine

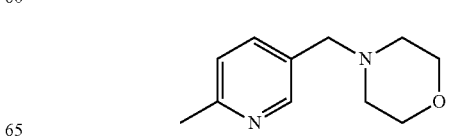

A compound of formula (VI)

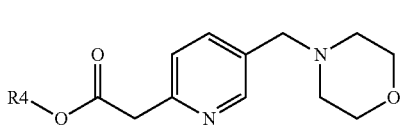
(VI)

wherein $R_4$ is $C_{1-12}$alkyl or aryl-$C_{1-4}$alkyl, particularly $C_{1-4}$alkyl, preferably ethyl.

A compound of formula (VIII)

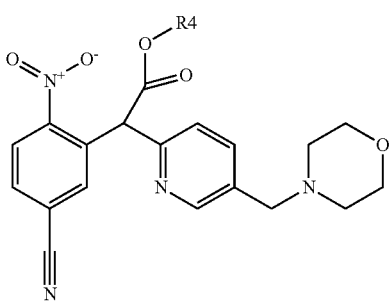
(VIII)

wherein $R_4$ is $C_{1-12}$alkyl or aryl-$C_{1-4}$alkyl, particularly $C_{1-4}$alkyl, preferably ethyl.

A compound of formula (IX)

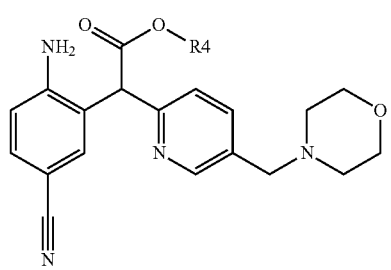
(IX)

wherein $R_4$ is $C_{1-12}$alkyl or aryl-$C_{1-4}$alkyl, particularly $C_{1-4}$alkyl, preferably ethyl.

A compound of formula (XII)

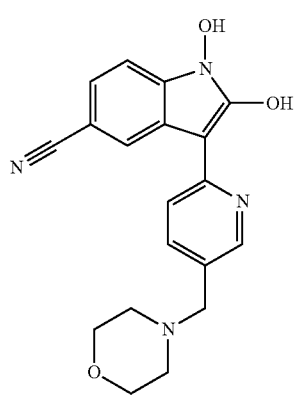
(XII)

A compound of formula (XIII)

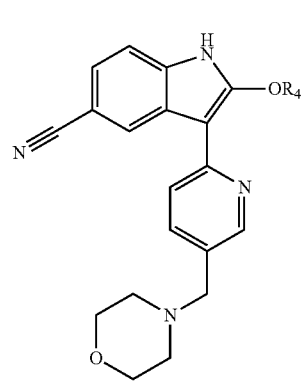
(XIII)

wherein $R_4$ is $C_{1-12}$alkyl or aryl-$C_{1-4}$ alkyl, particularly $C_{1-4}$alkyl, preferably ethyl.

A further aspect of the invention is a compound of formula (I)

(I)

obtainable by a process as described in claim 1.

Another aspect of the invention is a method of treatment of Bipolar Disorder by administration to a patient in need thereof a pharmaceutically effective amount of a compound of formula (I) prepared by the process according to claim 1.

The present invention is described in more detail in the following non-limiting Examples.

Preparation of the Compound of Formula (III), where R1 is Methanesulphonate

Synthesis of Methanesulfonic acid 6-methyl-pyridin-3-ylmethyl ester

Example 1

Methanesulfonic acid 6-methyl-pyridin-3-ylmethyl ester

To a solution of (6-Methyl-pyridin-3-yl)-methanol (24.36 kg, 198 mol) dissolved in tetrahydrofuran (80 kg) under nitrogen at −3° C. was added triethylamine (22.14 kg, 218.8 mol) over 30 mins followed by methanesulphonyl chloride (23.16 kg, 202.2 mol) over 3 hr and the slurry stirred for an additional 30 mins. The slurry was then filtered to remove triethylamine hydrochloride and the cake washed four times with tetrahydrofuran (21.6 kg). An aliquot was removed and concentrated and analysed.

¹H NMR (400 MHz; d6-DMSO): δ 8.5 (d, J=2.0 Hz, 1H), 7.70 (d, J=2.4 Hz, 1H), 7.30 (m, 1H), 4.78 (s, 2H), 3.5 (s, 3H), 2.3 (s, 3H) ppm; ¹³C NMR (100 MHz, d6-DMSO): δ 158.3, 149.3, 137.3, 131.0, 123.4, 43.7, 24.1 ppm.

Preparation of the Compound of Formula (V)

Synthesis of 4-(6-Methyl-pyridin-3-ylmethyl)-morpholine

Example 2

Synthesis of 4-(6-Methyl-pyridin-3-ylmethyl)-morpholine from methanesulfonic acid 6-methyl-pyridin-3-ylmethyl ester Morpholine (43.2 kg, 495.9 mol) was then added over 2 hrs to the solution of methanesulfonic acid 6-methyl-pyridin-3-ylmethyl ester (198 mol; Example 1) in tetrahydrofuran (161 kg) under nitrogen at 15-20° C. and the resulting slurry stirred for 19 hrs. The suspension was filtered through a Silica (15.5 kg) column and the cake washed five times with tetrahydrofuran (43.5 kg). 440 L of the solution was then removed under vacuum distillation and heptane (41.52 kg) added. This was repeated two more times followed by the addition of heptane (48.6 kg) and the solution filtered through a Celite® (4.08 kg) bed at 40° C. and the cake washed twice with heptane (7.2 kg). Then the filtrate cooled to 20° C. over 3 hrs then to −12° C. over 5 hrs and held for 12 hrs at −12° C. The suspension was filtered and the cake washed with cold (0° C.) heptane (8.5 kg) and then dryed at 25° C. under vacuum, which gave 25.44 kg, 67% yield of 4-(6-Methyl-pyridin-3-ylmethyl)-morpholine as a beige solid. ¹H NMR (400 MHz; CDCl₃): δ 8.4 (d, J=1.72 Hz, 1H), 7.54 (dd, J=2.1, 7.91 Hz, 1H), 7.1 (d, J=7.92 Hz, 1H), 3.68 (apparent t, J=4.6, 9.28 Hz, 4H), 3.4 (s, 2H), 2.5 (s, 3H), 2.4 (apparent t, J=4.5, 8.93 Hz, 4H); ¹³C NMR (100 MHz, CDCl₃): δ 157.3, 149.8, 137.2, 129.9, 122.9, 66.9, 60.3, 53.5, 24.1 ppm; MS (ESI) m/z 193 [M+1]⁺; Melting point: 51-52° C.

Example 3

Synthesis of, 4-(6-Methyl-pyridin-3-ylmethyl)-morpholine using iron (III) 2,4-pentanedionate and of methylmagnesium chloride To a solution of 4-(6-Chloro-pyridin-3-ylmethyl)-morpholine (212 g, 1 mol) in tetrahydrofuran (1.5 L) and N-methylpyrollidinone (318 ml) was added iron (III) 2,4-pentanedionate (35.2 g, 0.01 mol) and the mixture cooled to −5° C. under nitrogen. A solution of methylmagnesium chloride in tetrahydrofuran (498 ml, 3.0M, 1.5 mol) was added dropwise over 40 mins and after an additional 30 mins the reaction mixture was poured into a saturated aqueous ammonium chloride solution (1.7 L) at 0° C. The resulting biphasic solution was filtered through a Celite® plug. The filtrate was separated and the aqueous layer extracted with ethylacetate (600 ml). The combined organic layer was concentrated and diluted with ethylacetate (200 ml) then extracted with aqueous hydrochloric acid (10%, 200 ml). The acidic layer was separated and washed with ethylacetate, then cooled in an ice bath and basified to pH 11 with sodium carbonate (solid). Sodium chloride (125 g) was added to the aqueous layer which was then extracted twice with ethylacetate (300 ml). The combined organic layer was concentrated to a solid, which was dissolved in hexane (600 ml) at 50° C. then placed in the fridge at −5° C. overnight. Two crops were obtained, which gave a total of 126.6 g, 68% yield of 4-(6-Methyl-pyridin-3-ylmethyl)-morpholine as beige solid. ¹H NMR (400 MHz; CDCl₃): δ 8.4 (d, J=1.72 Hz, 1H), 7.54 (dd, J=2.1, 7.91 Hz, 1H), 7.1 (d, J=7.92 Hz, 1H), 3.68 (apparent t, J=4.6, 9.28 Hz, 4H), 3.4 (s, 2H), 2.5 (s, 3H), 2.4 (apparent t, J=4.5, 8.93 Hz, 4H); ¹³C NMR (100 MHz, CDCl₃): δ 157.3, 149.8, 137.2, 129.9, 122.9, 66.9, 60.3, 53.5, 24.1 ppm; MS (ESI) m/z 193 [M+1]⁺; Melting point: 51-52° C.

Example 4

Synthesis of, 4-(6-Methyl-pyridin-3-ylmethyl)-morpholine from 5-chloromethyl-2-methyl-pyridine To a solution of (6-methyl-3-pyridyl)-methanol (50 g, 0.506 mol) in toluene (500 ml) and water (9 ml) at 35° C. under nitrogen was added thionyl chloride (66.9 ml, 1.06 mol) dropwise After stirring at 35° C. overnight 300 ml was distilled off under vacuum and redilluted with toluene (250 ml) and water (10 ml) to give a solution of 5-chloromethyl-2-methyl-pyridine (J. Med. Chem, 2004, 47(11), 4787). The mixture was then heated to 40° C. and morpholine (112.2 ml, 1.29 mol) added and the slurry heated to 80° C. for 3 hrs. After cooling to room temperature saturated sodium carbonate solution (150 ml) was added and the aqueous phase separated and extracted with toluene (200 ml). The combined organic layer was washed with brine and concentrated. The oil was dissolved in iso-octane (300 ml) at 40° C. then cooled to −5° C. overnight. Two crops were obtained which gave 53.65 g, 72% yield of 4-[(6-methylpyridin-3-yl)methyl]morpholine as a beige solid. ¹H NMR (400 MHz; CDCl₃): δ 8.4 (d, J=1.72 Hz, 1H), 7.54 (dd, J=2.1, 7.91 Hz, 1H), 7.1 (d, J=7.92 Hz, 1H), 3.68 (apparent t, J=4.6, 9.28 Hz, 4H), 3.4 (s, 2H), 2.5 (s, 3H), 2.4 (apparent t, J=4.5, 8.93 Hz, 4H); ¹³C NMR: (100 MHz, CDCl₃): δ 157.3, 149.8, 137.2, 129.9, 122.9, 66.9, 60.3, 53.5, 24.1 ppm; MS (ESI) m/z 193 [M+1]⁺; Melting point: 51-52° C.

Preparation of the Compound of Formula (VI), where R4 is Ethyl

Synthesis of (5-morpholin-4-ylmethyl-pyridin-2-yl)-acetic acid ethyl ester

Example 5

(5-Morpholin-4-ylmethyl-pyridin-2-yl)-acetic acid ethyl ester 4-(6-Methyl-pyridin-3-ylmethyl)-morpholine (30 g, 156 mmol) and diethylcarbonate (23.96 g, 202.9 mmol) were dissolved in tetrahydrofuran (150 ml) under an inert atmosphere. The solution was cooled to −13° C. and lithium diisopropylamide solution (190.8 ml, 1.8M, 343.3 mmol) added dropwise over 1 hr 45 min. After stirring for an additional 35 min the reaction mixture was added to a cold aqueous solution of ammonium chloride (204.5 ml, 4.58M, 936.2 mmol) at 0° C. The biphasic mixture was warmed to 30° C. and separated. The aqueous layer was extracted twice with toluene (120 ml) and the combined organic layers were concentrated by vacuum distillation to give (5-Morpholin-4-ylmethyl-pyridin-2-yl)-acetic acid ethyl ester as a toluene solution (204 ml) (55.38 g, 92% yield (based on assay of 74.5 w/w %). An aliquot was removed and purified by column chromatography eluting with dichloromethane/methanol (40:1), which gave (5-morpholin-4-ylmethyl-pyridin-2-yl)-acetic acid ethyl ester as a yellow oil. ¹H NMR (400 MHz; CDCl₃,): δ 8.45 (d, J=1.88 Hz, 1H), 7.65 (dd, J=2.21, 7.93 Hz, 1H), 7.25 (d, J=6.12 Hz, 1H), 4.15 (q, J=7.17, 14.29 Hz, 2H), 3.82 (s, 2H), 3.69 (t, J=4.61, 9.28 Hz, 4H), 3.45 (s, 2H), 2.42 (t, J=4.52, 9.1 Hz, 4H), 1.25 (t, J=7.13, 14.29 Hz, 3H); $^{13}$C NMR: (100 MHz, CDCl$_3$): δ 170.7, 153.4, 150.1, 137.4, 131.6, 123.5, 66.9, 61.03, 60.3, 53.5, 43.6, 14.2 ppm; MS (ESI) m/z 265 [M+1]$^+$.

Example 6

(5-Morpholin-4-ylmethyl-pyridin-2-yl)-acetic acid ethyl ester using tetrahydrofuran as extractant 4-(6-Methyl-pyridin-3-ylmethyl)-morpholine (20 g, 104 mmol) and diethylcarbonate (12.4 g, 104 mmol) were dissolved in tetrahydrofuran (100 ml) under an inert atmosphere. The solution was cooled to −13° C. and lithium diisopropylamide solution (144 ml, 1.8M, 259 mmol) added dropwise over 2 hr 45 min. After stirring for an additional 30 min the reaction mixture was added to a cold aqueous solution of ammonium chloride (68.2 ml, 4.58M, 312.1 mmol) at 0° C. The biphasic mixture was warm to 30° C. and separated. The aqueous layer was extracted twice with tetrahydrofuran (80 ml) and the combined organic layers were concentrated under vacuum to give (5-Morpholin-4-ylmethyl-pyridin-2-yl)-acetic acid ethyl ester (27.20 g, 80% yield (based on 80.7 w/w % assay). (The crude product mixture is used in example 8). Characterisation data were in accordance with example 5. Preparation of the Compound of Formula (VIII), where R4 is Ethyl Synthesis of (5-Cyano-2-nitro-phenyl)-(5-morpholin-4-ylmethyl-pyridin-2-yl)-acetic acid ethyl ester hydrochloride salt Example 7

(5-Cyano-2-nitro-phenyl)-(5-morpholin-4-ylmethyl-pyridin-2-yl)-acetic acid ethyl ester using 3-fluoro-4-nitrobenzonitrile in tetrahydrofuran and toluene To a solution of (5-Morpholin-4-ylmethyl-pyridin-2-yl)-acetic acid ethyl ester (51.03 g, 74.5% w/w %, 143.8 mmol; Example 5) in toluene (204.1 ml) was added a solution of 3-fluoro-4-nitrobenzonitrile (24.5 g, 151 mmol) in tetrahydrofuran (357 ml) and the solution was degassed three times with nitrogen and then cooled to −20° C. Lithium tert-butoxide solution in tetrahydrofuran (137. ml, 20 w/w %, 302 mmol) was added dropwise over 1 hr. After stirring for an additional 1 hr 20 min the reaction mixture was then added to a cold aqueous solution of ammonium chloride (188 ml, 4.58M, 6862.7 mmol) at 0° C. The biphasic mixture was warmed to 30° C. and Celite® (76.5 g) added, then filtered. The filter cake was washed twice with toluene (153 ml) then the combined filtrate was separated and the organic layer washed twice with water (153 ml). The organic layer was concentrated by distillation to give (5-Cyano-2-nitro-phenyl)-(5-morpholin-4-ylmethyl-pyridin-2-yl)-acetic acid ethyl ester as a toluene solution (196 ml) (titration, HClO$_4$, assay 80.47 w/w %). The crude product mixture is directly used in the next step.

Synthesis of (5-Cyano-2-nitro-phenyl)-(5-morpholin-4-ylmethyl-pyridin-2-yl)-acetic acid ethyl ester hydrochloride salt in toluene and ethanol To the (5-Cyano-2-nitro-phenyl)-(5-morpholin-4-ylmethyl-pyridin-2-yl)-acetic acid ethyl ester solution in toluene (196 ml; Example 7) was added ethanol (394 ml) and the solution is heated to 60° C. A solution of hydrochloric acid in isopropanol (26.8 ml, 4.87M, 103.3 mol) was then added followed by addition of seeds (317 mg) and the solution cooled to −10° C. over 10 hrs. The crystals were filtered and washed three times with ethanol (63 ml). After drying at 40° C. under vacuum gave 48.62 g, 87% yield of (5-Cyano-2-nitro-phenyl)-(5-morpholin-4-ylmethyl-pyridin-2-yl)-acetic acid ethyl ester hydrochloride salt as red wine crystals.

$^1$H NMR (400 MHz; D$_2$O,): δ 8.54 (d, J=1.92, 1H), 8.17 (d, J=8.49, 1H), 7.97 (dd, J=2.24, 8.12 Hz, 1H), 7.89 (dd, J=1.68, 8.48 Hz, 1H), 7.50 (d, J=81 Hz, 1H), 7.46 (d, J=1.74 Hz, 1H), 4.37 (s, 2H), 4.16 (q, J=7.05, 14.25 Hz, 2H), 3.87 (br s, 4H), 3.28 (br s, 4H), 1.07 (t, J=7.16, 14.28 Hz, 3H), $^{13}$C NMR (100 MHz, D$_2$O): δ 171.6, 156.5, 151.4, 150.8, 141.5, 135.5, 133.5, 132.1, 126.2, 125.6, 124.5, 117.1, 116.7, 63.7, 63.4, 57.4, 51.4, 13.01 ppm; MS (ESI) m/z 411 [M+1]$^+$; Mpt 175° C. (decomp.).

Example 8

(5-Cyano-2-nitro-phenyl)-(5-morpholin-4-ylmethyl-pyridin-2-yl)-acetic acid ethyl ester using 3-fluoro-4-nitrobenzonitrile in tetrahydrofuran To a stirred solution of (5-Morpholin-4-ylmethyl-pyridin-2-yl)-acetic acid ethyl ester (20.7 g, 80.7 w/w %, 83 mmol; Example 6) in tetrahydrofuran (104 ml) was added 3-fluoro-4-nitrobenzonitrile (13.2 g, 78.3 mmol) and nitrogen gas is bubbled through the reaction solution and cooled to −20° C. Lithium tert-butoxide solution in tetrahydrofuran (76.8 ml, 20 w/w %, 186 mmol) was added dropwise over 1 hr 30 min. After stirring for an additional 40 mins at −10° C. the reaction mixture is added to a cold aqueous solution of sulphuric acid (208.8 ml, 0.45M, 94 mmol) at 0° C. To the mixture was added tert-butylmethyl ether (62 ml) and then warm to 30° C. with stirring. The aqueous acidic layer was separated and the organic layer extracted with aqueous sulphuric acid solution (34.8 m, 0.45M, 15.7 mmol).

To the combined acidic layers was added n-butylacetate (104 ml) and cooled to 0° C. Potassium carbonate solution (72.2 ml, 2.17M, 156.5 mmol) was added dropwise then the biphasic mixture heated to 30° C. and the organic layer separated and washed with water (41.4 ml). The organic layer was then concentrated by distillation to give (5-Cyano-2-nitro-phenyl)-(5-morpholin-4-ylmethyl-pyridin-2-yl)-acetic acid ethyl ester as an n-butylacetate solution (92 ml) (titration, HClO$_4$, 79.3 w/w %) The crude product mixture is directly used in the next step.

Synthesis of (5-Cyano-2-nitro-phenyl)-(5-morpholin-4-ylmethyl-pyridin-2-yl)-acetic acid ethyl ester hydrochloride salt in n-butylacetate and ethanol To the (5-Cyano-2-nitro-phenyl)-(5-morpholin-4-ylmethyl-pyridin-2-yl)-acetic acid ethyl ester solution in n-butylacetate (92 ml; Example 8) was added ethanol (235.3 ml) followed by n-butylacetate (117.7 ml) and the solution was heated to 60° C. Seed (0.1 g) was added to the hot solution followed by a solution of hydrochloric acid in isopropanol (13.44 ml, 4.68M, 62.9 mol) and the solution cooled to −10° C. over 10 hrs. The crystals were filtered and washed twice with ethanol (20 ml). After drying at 40° C. under vacuum gave 21.46 g, 79% yield of (5-Cyano-2-nitro-phenyl)-(5-morpholin-4-ylmethyl-pyridin-2-yl)-acetic acid ethyl ester hydrochloride salt as red wine crystals. Characterisation data were in accordance with example 7.

Isolation of (5-Cyano-2-nitro-phenyl)-(5-morpholin-4-ylmethyl-pyridin-2-yl)-acetic acid ethyl ester as the free base from n-butylacetate and heptane A solution of (5-Cyano-2-nitro-phenyl)-(5-morpholin-4-ylmethyl-pyridin-2-yl)-acetic acid ethyl ester (16.72 g with a strength of 94.7 w/w % (NMR)) in n-butylacetate (50 ml) was cooled to 0° C. followed by the addition of the seed (0.16 g). Heptane (84 ml) was then added slowly over 5 hrs and the mixture held at 0° C. for 1 hr then cooled to −5° C. over 3 hrs. After overnight stirring at −5° C. the suspension was then filtered and washed with a precooled (−5° C.) mixture of n-butyl acetate/heptane (22 ml/13 ml). Drying at 40° C. under vacuum gave 16.24 g, 70% yield of (5-Cyano-2-nitro-phenyl)-(5-morpholin-4-ylmethyl-pyridin-2-yl)-acetic acid ethyl ester as beige crystals. $^1$H NMR (400 MHz; CDCl$_3$,): δ 8.56 (d, J=1.83, 1H), 8.06 (d, J=8.40, 1H), 7.78 (d, J=1.68 Hz, 1H), 7.74 (dd, J=1.76, 8.4 Hz, 1H), 7.32 (d, J=7.92 Hz, 1H), 5.74 (s, 1H), 4.24 (m, 2H), 3.73 (br s, 4H), 3.56 (br s, 2H), 2.29 (br s, 4H), 1.24 (t, J=7.12, 14.24 Hz, 3H), $^{13}$C NMR (100 MHz, CDCl$_3$): δ 169.5, 154.3, 151.2, 150.6, 138.1, 136.4, 133.9, 131.9, 125.2, 124, 116.9, 116.7, 66.9, 62.2, 60.1, 54, 53.6, 14 ppm; MS (ESI) m/z 411 [M+1, Melting point 83-84° C.

Example 9

(5-Cyano-2-nitro-phenyl)-(5-morpholin-4-ylmethyl-pyridin-2-yl)-acetic acid ethyl ester hydrochloride salt, using 4-nitrobenzonitrile To a cold solution of (5-Morpholin-4-ylmethyl-pyridin-2-yl)-acetic acid ethyl ester (25 g, 130 mmol) and diethylcarbonate (33.79 g, 286 mmol) in tetrahydrofuran (62.5 ml) under nitrogen at −10° C. was added lithium diisopropylamide in tetrahydrofuran (158.9 ml, 1.8M, 286 mmol) dropwise over 1 hr 10 min. After stirring for an additional 30 mins at −10° C. a solution of 4-nitrobenzonitrile (29.78 g, 195 mmol) in tetrahydrofuran (175 ml) is added dropwise and stirring continued for 3 hrs. The reaction mixture was poured into a cold aqueous hydrochloric solution (375 ml, 2M) at 0° C.; after warming to room temperature the acidic aqueous layer was separated and washed with tert-butyl methyl ether (200 ml). The acidic aqueous layer was cooled in an ice bath and tert-butyl methyl ether (500 ml) was added. The mixture was then made basic (pH 9) by addition of sodium carbonate solution (55 ml, 25 w/w %). The mixture was then warmed to room temperature and the organic phase separated; the basic aqueous phase was extracted with tert-butyl methyl ether (250 ml). The combined organic layer was treated with Celite® (12.5 g), then filtered and the filtrate concentrated in vacuo to give (5-Cyano-2-nitro-phenyl)-(5-morpholin-4-ylmethyl-pyridin-2-yl)-acetic acid ethyl ester crude (28.58 g, 51% w/w %). The crude material was dissolved in ethanol (300 ml) then heated to 40° C. and a solution of hydrochloric acid in isopropanol (8 ml, 4.95M, 20.7 mmol) was added followed by addition of seeds (90 mg) and the solution cooled to −10° C. over 10 hrs. The crystals were filtered and washed with tert-butyl methyl ether. After drying at 40° C. under vacuum gave 14.51 g, 25% yield of (5-Cyano-2-nitro-phenyl)-(5-morpholin-4-ylmethyl-pyridin-2-yl)-acetic acid ethyl ester hydrochloride salt as red wine crystals. Characterisation data were in accordance with example 7.

Preparation of the Compound of Formula (IX), where R4 is Ethyl

The synthesis of (2-amino-5-cyano-phenyl)-(5-morpholin-4-ylmethyl-pyridin-2-yl)-acetic acid ethyl ester Example 10

(2-Amino-5-cyano-phenyl)-(5-morpholin-4-ylmethyl-pyridin-2-yl)-acetic acid ethyl ester in toluene and dimethylformamide (5-Cyano-2-nitro-phenyl)-(5-morpholin-4-ylmethyl-pyridin-2-yl)-acetic acid ethyl ester hydrochloride salt (100 g, 223.7 mmol) was slurried in toluene at room temperature and a solution of sodium hydrogen carbonate (47 g, 559 mmol) in water (500 ml) was added and the reaction mixture stirred at room temperature for 45 mins. The organic phase was separated and washed twice with water (500 ml) then concentrated by distillation under vacuum to 229 ml. Dimethylformamide (846 ml) was then added followed by Degussa® [CF1082 RV/W®; Platinum (3%) and Vanadium (0.6%)] on active carbon (20 g, 20 w/w %) and the reaction mixture degassed with nitrogen followed by heating to 40° C. then hydrogen (g) was added to a pressure of 3-4 bar g and left for 30 min then heated to 70° C. and stirred for 6 hrs under an atmosphere of hydrogen. After cooling to room temperature the reaction mixture was purged with nitrogen and the catalyst filtered off and the filtrate concentrated to 395 ml. (The solution was used in the next step; Example 12). An aliquot was taken out and purified by column chromatography on silica eluting with dichloromethane/methanol (1% ammonium hydroxide) (25:1) gave (2-Amino-5-cyano-phenyl)-(5-morpholin-4-ylmethyl-pyridin-2-yl)-acetic acid ethyl ester as a pale orange oil.
$^1$H NMR (400 MHz; CDCl$_3$): δ 8.46 (d, J=1.73 Hz, 1H), 7.68 (dd, J=1.96, 8.08 Hz, 1H), 7.50 (d, J=1.89 Hz, 1H), 7.35 (br d, J=8.2 Hz, 2H), 6.64 (d, J=8.37 Hz, 1H), 5.07 (s, 1H), 5.01 (s, 2H), 4.26 (q, J=7.16, 14.29 Hz, 2H), 3.70 (t, J=4.64, 9.2 Hz, 4H), 3.48 (s, 2H), 2.44 (t, J=3.79, 8.4 Hz, 4H), 1.25 (t, J=7.13, 14.29 Hz, 3H); $^{13}$C NMR: (100 MHz, CDCl$_3$) δ 170.8, 155.8, 149.6, 149.3, 138.0, 133.6, 132.7, 123.1, 122.5, 120.0, 116.5, 101.2, 66.9, 61.8, 60.2, 56.0, 53.5, 14.1 ppm; MS (ESI) m/z [M+1]$^+$ 381.

Example 11

(2-Amino-5-cyano-phenyl)-(5-morpholin-4-ylmethyl-pyridin-2-yl)-acetic acid ethyl ester in n-butylacetate (5-Cyano-2-nitro-phenyl)-(5-morpholin-4-ylmethyl-pyridin-2-yl)-acetic acid ethyl ester hydrochloride salt (50 g, 111.9) was slurried in n-butylacetate (500 ml) at room temperature and a solution of sodium hydrogen carbonate (23.5 g, 279.7 mmol) in water (250 ml) was added and the reaction mixture stirred at room temperature for 1 hr. The organic phase was separated and washed with water (250 ml). Degussa® [CF1082 RV/W®; Platinum (3%) and Vanadium (0.6%)] on active carbon (10 g, 20 w/w %) was added to the n-butylacetate solution and the reaction mixture degassed with nitrogen followed by heating to 40° C. then hydrogen (g) was added to a pressure of 3-4 bar g and left for 30 min then heated to 70° C. and stirred for 2 hrs 30 min under an atmosphere of hydrogen. After cooling to room temperature the reaction mixture was purge with nitrogen and the catalyst filtered off and the catalyst washed with n-butylacetate (100 ml). The filtrate was concentrated to 130 ml. (The solution was used in example 13). Characterisation data were in accordance with example 10.

Preparation of the Compound of Formula (I)

Synthesis of 2-hydroxy-3-[5-(morpholin-4-ylmethyl) pyridin-2-yl]1H-indole-5-carbonitrile citrate Example 12

2-Hydroxy-3-[5-(morpholin-4-ylmethyl)pyridin-2-yl]1H-indole-5-carbonitrile citrate in dimethylformamide and toluene To the (2-Amino-5-cyano-phenyl)-(5-morpholin-4-ylmethyl-pyridin-2-yl)-acetic acid ethyl ester solution (395 ml, Example 10) was added dimethylformamide (84.6 ml) and toluene (275.5 ml). The mixture was then heated to 60° C. and a hot solution of citric acid monohydrate (47 g, 223.75 mmol) in iso-propanol (137.5 ml) at 50° C. was added Then the reaction mixture heated to 90° C. Seed (1.0 g, 1 w/w %) was then added followed by a hot solution of citric acid monohydrate (47 g, 223.75 mmol) in iso-propanol (137.5 ml) at 50° C. and the reaction slurry stirred for 2 hours then cool to 5° C. over 6 hrs. After stirring for 20 hrs at 5° C. the slurry is filtered and washed with toluene/dimethylformamide (63.5 ml/25.9 ml), followed by isopropanol (203.5 ml) twice. After drying at 50° C. under vacuum gave 101.85 g; (96.3 w/w % assay), 83% yield of 2-hydroxy-3-[5-(morpholin-4-ylmethyl)pyridin-2-yl]1H-indole-5-carbonitrile citrate as an orange solid. $^1$H NMR (d6-DMSO, 400 MHz): δ 14.7 (br s, 1H), 10.88 (s, 1H), 9.66 (br s, 3H), 8.08 (s, 1H), 7.88 (s, 1H), 7.78 (s, 2H), 7.27 (dd, J=1.36, 8.01 Hz, 1H), 7.00 (d, J=8.0 Hz, 1H), 3.59 (m, 4H), 3.49 (s, 2H), 2.89 (s, DMF), 2.77 (s, 0.7H), 2.74 (s, 1.3H), 2.72 (s, DMF), 2.68 (s, 1.3H), 2.64 (s, 0.7H), 2.50 (m, 4H) ppm; $^{13}$C NMR (d6-DMSO, 100 MHz): δ 175.6, 171.9, 169.2, 162.8 (DMF), 148.9, 142.5, 137.8, 137.6, 137.0, 129.3, 128.6, 125.7, 124.6, 121.5, 121.2, 119.3, 118.8, 109.3, 101.9, 85.2, 72.8, 66.1, 62.5, 58.4, 52.8, 43.5, 36.2 (DMF), 31.2 (DMF), 21.4 ppm; MS (ESI) m/z [M+1]$^+$ 335.

Example 13

2-Hydroxy-3-[5-(morpholin-4-ylmethyl)pyridin-2-yl]1H-indole-5-carbonitrile citrate in n-butylacetate/dimethylformamide To the (2-Amino-5-cyano-phenyl)-(5-morpholin-4-ylmethyl-pyridin-2-yl)-acetic acid ethyl ester solution in n-butyl acetate (130 ml, Example 11) was added n-butylacetate (55 ml) and dimethylformamide (90 ml) then heated to 60° C. and a hot solution of citric acid monohydrate (32.9 g, 156.63 mmol) in iso-propanol (210 ml) at 50° C. was added then the reaction mixture heated at 75° C. Seed (0.29 g) was then added and the mixture heated 90° C. The resulting slurry was stirred for 2 hours at 90° C. then cooled to 5° C. over 10 hrs and held overnight at 5° C. The slurry was filtered and washed with isopropanol (54.2 ml) twice. After drying at 50° C. under vacuum gave 53.80 g; (89.7 w/w % assay), 75% yield of 2-hydroxy-3-[5-(morpholin-4-ylmethyl)pyridin-2-yl]1H-indole-5-carbonitrile citrate as an orange solid. Characterisation data were in accordance with example 12.

Example 14

2-Hydroxy-3-[5-(morpholin-4-ylmethyl)pyridin-2-yl]1H-indole-5-carbonitrile citrate 2-Hydroxy-3-[5-(morpholin-4-ylmethyl)pyridin-2-yl]1H-indole-5-carbonitrile citrate (10 g, 19 mmol; Example 12) was dissolved in water (160 ml) at 90° C. and activated carbon (2.5 g, 25 w/w %) added. The mixture was stirred for 6 hrs then filtered hot. Ethanol (130 ml) was then added to the filtrate at 78° C. After cooling to 20° C. over 9 hrs the slurry was filtered and washed with ethanol/water followed by ethanol. After drying at 50° C. under vacuum gave 7.0 g, (96.2% w/w assay), 67% yield of 2-hydroxy-3-[5-(morpholin-4-ylmethyl)pyridin-2-yl]1H-indole-5-carbonitrile citrate as a yellow powder having a purity of at least 98%. The platinum and vanadium content were less than 10 ppm. $^1$H NMR (d6-DMSO, 400 MHz): δ 14.7 (br s, 1H), 10.86 (s, 1H), 9.66 (br s, 3H), 8.09 (s, 1H), 7.89 (s, 1H), 7.77 (s, 2H), 7.27 (dd, J=1.36, 8.01 Hz, 1H), 7.00 (d, J=8.0 Hz, 1H), 3.59 (t, J=4.41, 8.84 Hz, 4H), 3.47 (s, 2H), 2.77 (s, 0.7H), 2.74 (s, 1.3H), 2.66 (s, 1.3H), 2.62 (s, 0.7H), 2.47 (m, 4H) ppm; $^{13}$C NMR (d6-DMSO, 100 MHz): δ 175.4, 171.8, 169.2, 148.9, 142.6, 137.6, 136.8, 125.7, 124.7, 121.5, 119.4, 118.8, 109.3, 101.6, 85.1, 72.8, 66.2, 58.6, 53.0, 43 ppm; MS (ESI) m/z [M+1]$^+$ 335.

Example 15

2-Hydroxy-3-[5-(morpholin-4-ylmethyl)pyridin-2-yl]1H-indole-5-carbonitrile using triethylamine To a solution of (2-Amino-5-cyano-phenyl)-(5-morpholin-4-ylmethyl-pyridin-2-yl)-acetic acid ethyl ester solution in n-butyl acetate (10 ml, 0.16M, 1.6 mmol) was added triethylamine (0.25 ml, 1.8 mmol) and the mixture heated to 90° C. and stirred overnight. The resulting slurry was cooled to 0° C. and then filtered and washed with tertbutyl methyl ether (20 ml). After drying at 50° C. under vacuum gave 0.26 g; 49% yield of 2-hydroxy-3-[5-(morpholin-4-ylmethyl)pyridin-2-yl]1H-indole-5-carbonitrile as an orange solid. $^1$H NMR (400 MHz; CDCl$_3$,): δ 14.76 (br s, 1H), 10.9 (s, 1H), 8.07 (s, 1H), 7.88 (s, 1H), 7.77 (m, 2H), 7.26 (dd, J=1.08, 7.97 Hz, 1H), 7.00 (d, J=8.0 Hz, 1H), 3.55 (m, 4H), 3.35 (s, 2H), 2.35 (br s, 4H); $^{13}$C NMR: (100 MHz, CDCl$_3$): δ 169.2, 148.9, 142.5, 1367.5, 136.4, 125.7, 124.5, 122.8, 121.8, 121.5, 119.3, 118.8, 101.8, 84.9, 66.6, 58.8, 53.3 ppm; MS (ESI) m/z [M+1]$^+$ 335.

Preparation of the Compound of Formula (XII)

Synthesis of 1,2-Dihydroxy-3-(5-morpholin-4-ylmethyl-pyridin-2-yl)-1H-indole-5-carbonitrile Example 16

1,2-Dihydroxy-3-(5-morpholin-4-ylmethyl-pyridin-2-yl)-1H-indole-5-carbonitrile (5-Cyano-2-nitro-phenyl)-(5-morpholin-4-ylmethyl-pyridin-2-yl)-acetic acid ethyl ester HCl (8.0 g, 17.9 mmol was slurried in toluene (80 ml) at room temperature and sodium hydrogen carbonate (7.52 g, 89.5 μmol) dissolved in water (50 ml) was added and the reaction mixture stirred at room temperature for 25 min. The organic phase was separated and washed with water and then concentrated to dryness and then redissolved in ethanol (80 ml) and the solution added to a preheated solution of ammonium sulphide (26 ml, 21 w/w %, 107.4 mmol) in water at 50° C. over 20 mins. The resulting yellow slurry was stirred for 1 hr at 50° C. then cooled in an ice bath. The slurry was filtered and washed with water followed by isopropanol. After drying at 50° C. under vacuum gave a yellow powder, 6.67 g, (purity 94%), 76% yield of 1,2-Dihydroxy-3-(5-morpholin-4-ylmethyl-pyridin-2-yl)-1H-indole-5-carbonitrile. $^1$H NMR (400 MHz; d6-DMSO,):

δ 14.36 (br s, 1H), 10.86 (br s, 1H), 8.12 (s, 1H), 7.96 (s, 1H), 7.88 (br d, 1H), 7.87 (br d, 1H), 7.78 (br dd, 1H), 7.36 (dd, J=1.0, 8.0 Hz, 1H), 7.08 (d, H=8.1 Hz, 1H), 3.56 (t, J=4.0, 8.2 Hz, 4H), 3.37 (s, 2H), 2.27 (br s, 4H); $^{13}$C NMR: (100 MHz, d6-DMSO): δ 163.8, 148.8, 142.7, 136.7, 136.1, 123.1, 121.5, 120.4, 119.4, 119.1, 102.0, 81.9, 67.2, 66.6, 58.8, 53.3 ppm; MS (ESI) m/z [M+1]$^{+}$ 351.

Preparation of the Compound of Formula (I)

Synthesis of 2-hydroxy-3-[5-(morpholin-4-ylmethyl)pyridin-2-yl]1H-indole-5-carbonitrile Example 17

2-Hydroxy-3-[5-(morpholin-4-ylmethyl)pyridin-2-yl]1H-indole-5-carbonitrile

To a solution of 1,2-Dihydroxy-3-(5-morpholin-4-ylmethyl-pyridin-2-yl)-1H-indole-5-carbonitrile (1.0 g, 94% pure, 10.73 mmol) in acetic acid (60 ml) at 60° C. was added iron powder (1.8 g, 32.19 mmol) and the resulting dark green solution stirred at 60° C. for 3 hrs. The suspension was removed from the oil bath and cooled to room temperature. Celite® (10 g) was added and the mixture concentrated to dryness. The mixture was then purified by silica column chromatography eluting with dichloromethane/methanol (1% ammonium hydroxide) 5:1 to give an orange solid; which was reslurried with isopropanol, filtered and then washed with isopropanol. After drying at 50° C. under vacuum gave, 2.89 g, 81% yield of 2-Hydroxy-3-[5-(morpholin-4-ylmethyl)pyridin-2-yl]1H-indole-5-carbonitrile as a yellow powder. $^{1}$H NMR (400 MHz; CDCl$_3$,): δ 14.76 (br s, 1H), 10.9 (s, 1H), 8.07 (s, 1H), 7.88 (s, 1H), 7.77 (m, 2H), 7.26 (dd, J=1.08, 7.97 Hz, 1H), 7.00 (d, J=8.0 Hz, 1H), 3.55 (m, 4H), 3.35 (s, 2H), 2.35 (br s, 4H); $^{13}$C NMR: (100 MHz, CDCl$_3$): δ 169.2, 148.9, 142.5, 1367.5, 136.4, 125.7, 124.5, 122.8, 121.8, 121.5, 119.3, 118.8, 101.8, 84.9, 66.6, 58.8, 53.3 ppm; MS (ESI) m/z [M+1]$^{+}$ 335.

Preparation of the Compound of Formula (XIII), where R4 is Ethyl

Synthesis of 2-ethoxy-3-(5-morpholin-4-ylmethyl-pyridin-2-yl)-1H-indole-5-carbonitrile Example 18

2-Ethoxy-3-(5-morpholin-4-ylmethyl-pyridin-2-yl)-1H-indole-5-carbonitrile

To a solution of (2-Amino-5-cyano-phenyl)-(5-morpholin-4-ylmethyl-pyridin-2-yl)-acetic acid ethyl ester (1.2 g, 3.15 mmol) in toluene (2 ml) and dimethylformamide (10 ml) at room temperature was added a solution of hydrochloric acid in isopropanol (1.20 ml, 4.65M, 6.31 mmol) and the resulting suspension stirred for 1 hr. HPLC showed full conversion of (2-Amino-5-cyano-phenyl)-(5-morpholin-4-ylmethyl-pyridin-2-yl)-acetic acid ethyl ester with 6% of 2-ethoxy-3-(5-morpholin-4-ylmethyl-pyridin-2-yl)-1H-indole-5-carbonitrile (The crude product mixture was used in the next step; Example 19). An aliquot was removed and purified by column chromatography eluting with dichloromethane/methanol (1% ammonium hydroxide) 5:1 to give 2-ethoxy-3-(5-morpholin-4-ylmethyl-pyridin-2-yl)-1H-indole-5-carbonitrile as a pale brown solid. $^{1}$H NMR (400 MHz; d6-DMSO): δ 12.1 (br s, 1H), 8.88 (d, J=0.88 Hz, 1H), 8.51 (d, J=1.72 Hz, 1H), 7.88 (d, J=8.48 Hz, 1H), 7.65 (dd, J=2.24, 8.37 Hz, 1H), 7.44 (br d, J=7.85 Hz, 1H), 7.41 (dd, J=1.56, 5.93 Hz, 1H), 4.47 (q, J=6.96, 13.97 Hz, 2H), 3.59 (t, J=4.49, 9.01 Hz, 4H), 3.45 (s, 2H), 2.36 (br s, 4H), 1.47 (t, J=6.96, 13.96 Hz, 3H); $^{13}$C NMR (100 MHz, d6-DMSO): δ 153.6, 153.2, 149.8, 137.2, 133.6, 128.4, 126.6, 126.1, 123.4, 121.4, 120.1, 112.0, 102.6, 95.1, 68.2, 66.6, 60.0, 53.5, 15.32 ppm; MS (ESI) m/z [M+1]$^{+}$ 363.

Preparation of the Compound of Formula (I)

Synthesis of 2-hydroxy-3-[5-(morpholin-4-ylmethyl)pyridin-2-yl]1H-indole-5-carbonitrile hydrochloride salt Example 19

2-Hydroxy-3-[5-(morpholin-4-ylmethyl)pyridin-2-yl]1H-indole-5-carbonitrile hydrochloride salt The rest of the reaction mixture from Example 18 was heated to 90° C. and stirred overnight. The yellow slurry was cooled to room temperature and filtered. The crystals were washed twice with isopropanol then placed in an oven at 50° C. under vacuum which gave 0.72 g, 62% yield of 2-hydroxy-3-[5-(morpholin-4-ylmethyl)pyridin-2-yl]1H-indole-5-carbonitrile hydrochloride salt. $^{1}$H NMR (d6-DMSO, 400 MHz): δ 14.8 (br s, 1H), 11.55 (s, 1H), 10.98 (s, 1H), 8.31 (s, 1H), 8.08 (dd, J=1.92, 9.20 Hz, 1H), 8.01 (s, 1H), 7.89 (d, J=9.30 Hz, 1H), 7.31 (dd, J=6.60, 8.04 Hz, 1H), 7.02 (d, J=8.0 Hz, 1H), 4.28 (s, 2H), 3.94 (m, 2H), 3.81 (m, 2H), 3.31 (m, 2H), 3.08 (m, 2H); MS (ESI) m/z [M+1]$^{+}$ 335.

The invention claimed is:

1. A process for the manufacturing of a compound of formula (I), 2-hydroxy-3-[5-(morpholin-4-ylmethyl)pyridin-2-yl]1H-indole-5-carbonitrile, as a free base or a pharmaceutically acceptable salts thereof, by

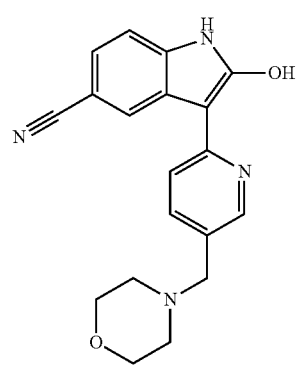

(I)

a) reacting a compound of formula (II)

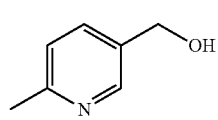

(II)

with a compound of formula R$_6$SO$_2$X wherein R$_6$ is C$_1$-C$_4$alkyl, C$_1$-C$_4$alkylphenyl, phenyl, phenylmethyl, halophenyl, nitrophenyl or CF$_3$, and X is halogen, particularly chloro, in the presence of a solvent and a base to give a compound of formula (III), wherein R$_1$ is R$_6$SO$_3$, where $R_6$ is $C_1$-$C_4$alkyl, $C_1$-$C_4$alkylphenyl, tolyl, phenyl, phenylmethyl, halophenyl, nitrophenyl or $CF_3$,

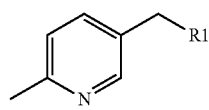

(III)

which is followed by bi) reacting the compound of formula (III) wherein $R_1$ is as defined above in the presence of morpholine optionally with a base and in a solvent to obtain a compound of formula (V)

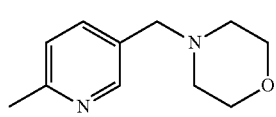

(V)

which is followed directly by step c) below, or alternatively bii) reacting a compound of formula (IV), wherein $R_2$ is methyl and $R_3$ is a halogen

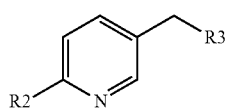

(IV)

in a solvent with morpholine optionally with a base to obtain compound of formula (V), or alternatively biii) reacting a compound of formula (IV) wherein $R_2$ is halogen and $R_3$ is morpholine attached at nitrogen

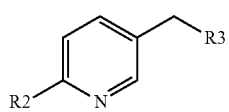

(IV)

with methylmagnesium halide in the presence of iron (2,4-pentanedionate)$_3$ in a solvent to obtain a compound with formula (V), followed by, c) reacting a compound of formula (V) with a carbonate of formula (X) wherein $R_4$ is independently selected from an $C_{1-12}$alkyl or aryl-$C_{1-4}$alkyl group, or a dicarbonate of formula (XI) wherein $R_7$ is a tert-butyl group

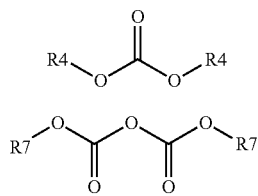

(X)

(XI)

in a solvent in the presence of a base to give a compound of formula (VI) wherein $R_4$ is independently selected from an $C_{1-12}$alkyl or aryl-$C_{1-4}$alkyl group

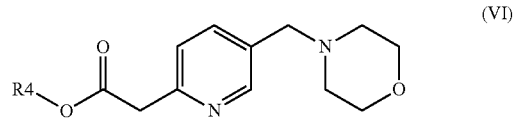

(VI)

which either is isolated, or its enolate is reacted further by, d) reacting the compound of formula (VI) wherein $R_4$ is $C_{1-12}$alkyl or aryl-$C_{1-4}$alkyl with a compound of formula (VII), wherein $R_5$ is a hydrogen or a halogen

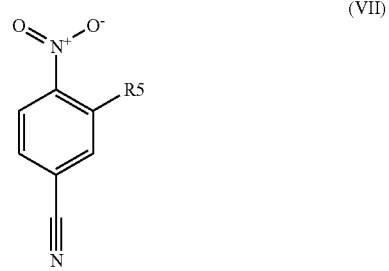

(VII)

in the presence of a base and a solvent, to form a compound of formula (VIII) wherein $R_4$ is $C_{1-12}$alkyl or aryl-$C_{1-4}$ alkyl

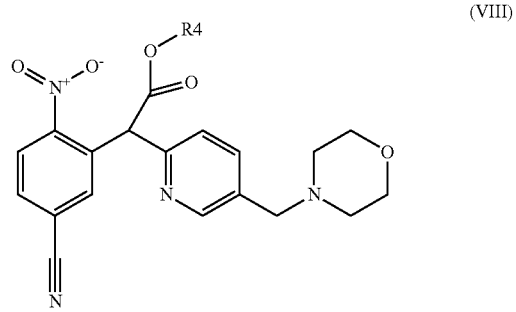

(VIII)

followed by, e) reducing the compound of formula (VIII) with a suitable reducing agent in the presence of a solvent to selectively reduce the nitro group to an amine in the presence of the other functional groups to obtain a compound of formula (IX) wherein $R_4$ is $C_{1-12}$alkyl or aryl-$C_{1-4}$alkyl,

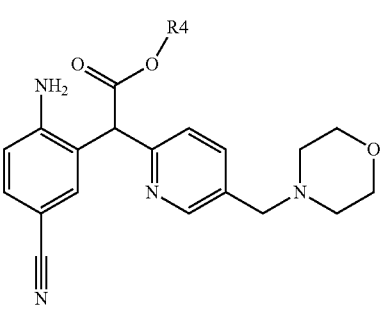

(IX)

followed by f) cyclisation the compound of formula (IX) with an acid to obtain a compound of formula (I), as a free base or a pharmaceutically acceptable salt thereof, or alternatively, h) reducing the compound of formula (VIII) with a suitable reducing agent in the presence of a solvent to obtain a compound of formula (XII)

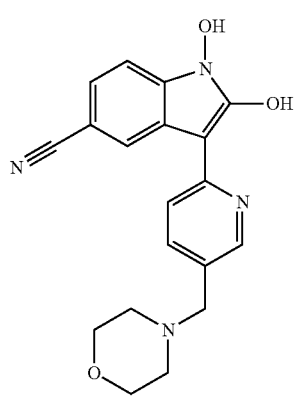

followed by k) reducing the compound of formula (XII) with a suitable reducing agent in the presence of a solvent to obtain a compound of formula (I), as a free base or a pharmaceutically acceptable salt thereof, or alternatively, l) reacting the compound of formula (IX) wherein $R_4$ is a $C_{1-12}$alkyl or aryl-$C_{1-4}$-alkyl with a suitable acid in a solvent to obtain a compound of formula (XIII), wherein $R_4$ is a $C_{1-12}$alkyl or aryl-$C_{1-4}$alkyl,

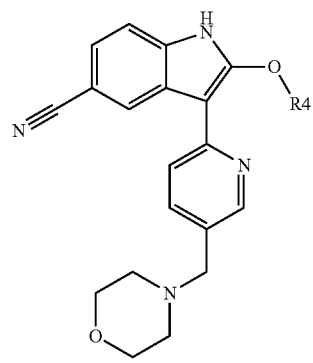

followed by m) reaction of the compound of formula (XIII) with a suitable acid in a solvent, to obtain a compound of formula (I), as a free base or a pharmaceutically acceptable salt thereof, the obtained free base or a pharmaceutically acceptable salt thereof, may optionally be further purified and isolated to obtain the pure free base or pharmaceutically acceptable salt thereof.

2. A process for preparation of a compound of formula (VIII) wherein $R_4$ is $C_{1-12}$alkyl or aryl-$C_{1-4}$alkyl

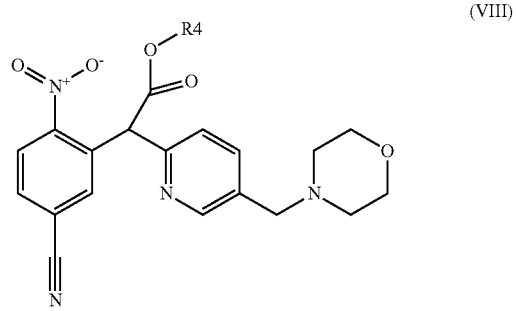

by reacting a compound of formula (VI) wherein $R_4$ is $C_{1-12}$alkyl or aryl-$C_{1-4}$alkyl

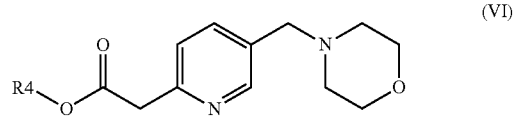

with a compound of formula (VII), wherein $R_5$ is a hydrogen or a halogen

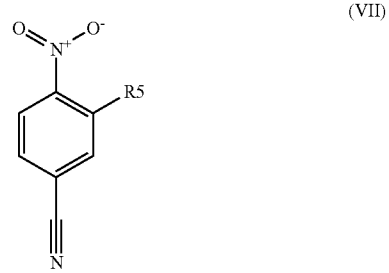

in the presence of a base and a solvent.

3. A process according to claim 1 wherein $R_5$ in a compound of formula (VII) is hydrogen or fluoro.

4. A process for the preparation of a compound of formula (IX) wherein $R_4$ is $C_{1-12}$alkyl or aryl-$C_{1-4}$alkyl

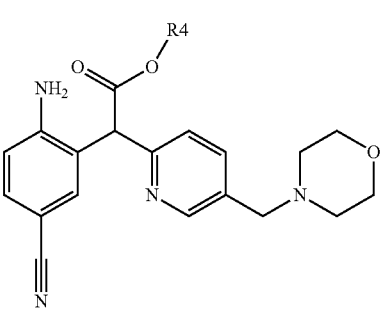

by selectively reducing the nitro group on the compound of formula (VIII)

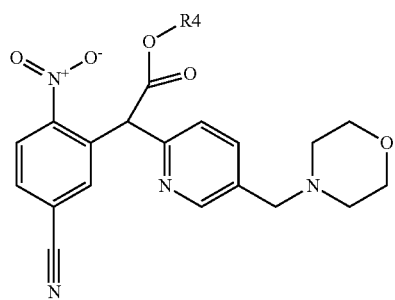

to an amine with a suitable reducing agent in the presence of a solvent.

5. A compound selected from:
a compound of formula (VI),

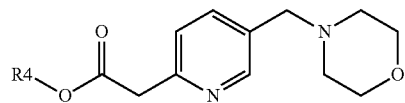

wherein $R_4$ is $C_{1-12}$alkyl or aryl-$C_{1-4}$alkyl;
a compound of formula (VIII)

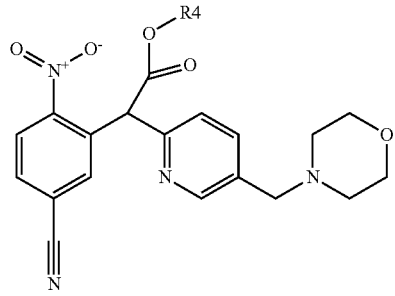

wherein $R_4$ is $C_{1-12}$alkyl or aryl-$C_{1-4}$alkyl, or
a compound of formula (IX)

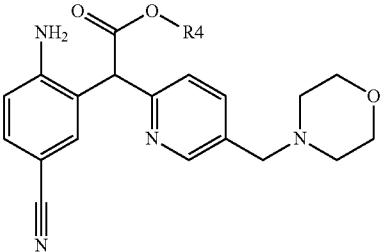

wherein $R_4$ is $C_{1-12}$alkyl or aryl-$C_{1-4}$alkyl.

6. A compound according to claim 5 wherein $R_4$ is $C_{1-4}$alkyl.

7. A compound of formula (XII)

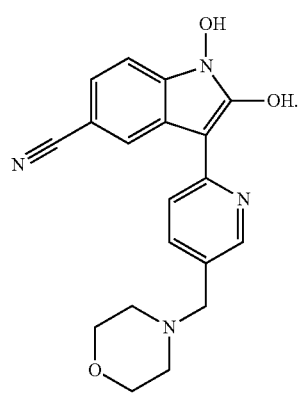

8. A process according to claim 2, wherein, in step d) $R_5$ in a compound of formula (VII) is hydrogen or fluoro.

* * * * *